US007811982B2

(12) United States Patent
McTavish

(10) Patent No.: US 7,811,982 B2
(45) Date of Patent: *Oct. 12, 2010

(54) COMPOUNDS AND METHODS FOR TREATING CANCER

(75) Inventor: Hugh McTavish, Birchwood, MN (US)

(73) Assignee: IGF Oncology, LLC, Birchwood, MN (US)

( * ) Notice: Subject to any disclaimer, the term of this patent is extended or adjusted under 35 U.S.C. 154(b) by 770 days.

This patent is subject to a terminal disclaimer.

(21) Appl. No.: 11/407,590

(22) Filed: Apr. 20, 2006

(65) Prior Publication Data

US 2006/0258569 A1 Nov. 16, 2006

Related U.S. Application Data

(63) Continuation-in-part of application No. PCT/US2004/034704, filed on Oct. 21, 2004.

(60) Provisional application No. 60/513,048, filed on Oct. 21, 2003.

(51) Int. Cl.
*A61K 38/00* (2006.01)
*A61K 38/16* (2006.01)
*C07K 5/00* (2006.01)

(52) U.S. Cl. .................. 514/2; 530/350; 424/198.1

(58) Field of Classification Search ...................... None
See application file for complete search history.

(56) References Cited

U.S. PATENT DOCUMENTS

| | | | | |
|---|---|---|---|---|
| 4,876,242 | A | * | 10/1989 | Applebaum et al. ............. 514/3 |
| 4,975,278 | A | * | 12/1990 | Senter et al. ............. 424/178.1 |
| 5,122,368 | A | | 6/1992 | Greenfield et al. |
| 5,444,045 | A | * | 8/1995 | Francis et al. ................. 514/12 |
| 5,518,888 | A | * | 5/1996 | Waldman .................... 435/7.23 |
| 2003/0092631 | A1 | * | 5/2003 | Deshayes et al. ............. 514/14 |
| 2003/0138430 | A1 | | 7/2003 | Stimmel et al. |
| 2004/0023887 | A1 | | 2/2004 | Pillutla et al. |
| 2004/0038303 | A1 | | 2/2004 | Unger |
| 2004/0137071 | A1 | | 7/2004 | Unger |
| 2004/0142381 | A1 | | 7/2004 | Hubbard et al. |

FOREIGN PATENT DOCUMENTS

| | | |
|---|---|---|
| WO | WO88/08715 | 11/1988 |
| WO | WO 93/21939 | 11/1993 |
| WO | WO 01/93900 | 12/2001 |
| WO | WO 02/49672 A2 | 6/2002 |
| WO | WO 03/074551 A2 | 9/2003 |

OTHER PUBLICATIONS

Laakoki et al, J Biol Chem, vol. 275, p. 10009-15, 2000.*
Laakoki et al, FEBS, vol. 420, p. 97-102, 1997.*
sequence alignment, 2009.*
sequence search result, 2010.*
Carlsson et al Biochem J. vol. 173, p. 723-737, 1978.*
seqeunce search result ID No. 4 and 9, 2009.*
seqeunce search result-1 (application '627), 2009.*
seqeunce search result-2 (application '623), 2009.*
Sequence alignment, 2009.*
Grothey, A. et al., 1999. The role of insulin-like growth factor I and its receptor in cell growth, transformation, apoptosis, and chemoresistance in solid tumors. J. Cancer Res. Clin. Oncol. 125:166-173.
Ayre SG, Garcia y Bellon DP, Garcia DP Jr. 2000. Insulin, chemotherapy, and the mechanisms of malignancy: the design and the demise of cancer, *Medical Hypotheses* 55:330-334.
Abita JP, Gauville C, Balitrand N, Gespach C, Canivet J. 1984, Binding of 125I-insulin to the human histiocytic lymphoma cell line U-937: effect of differentiation with retinoic acid. *Leuk Res.* 8(2):213-21.
Alabaster O, Vonderhaar BK, Shafie SM. 1981. Metabolic modification by insulin enhances methotrexate cytotoxicity in MCF-7 human breast cancer cells. *Eur J Cancer Clin Oncol.* 17(11):1223-8.
Schilsky RL, Bailey BD, Chabner BA. 1981. Characteristics of membrane transport of methotrexate by cultured human breast cancer cells. *Biochem Pharmacol.* 30(12):1537-42.
Oster JB, Creasey WA. 1981. Enhancement of cellular uptake of ellipticine by insulin preincubation. *Eur J Cancer Clin Oncol.* 17(10):1097-103.
Daughaday WH, Rotwein P. 1989. Insulin-like growth factors I and II. Peptide, messenger ribonucleic acid and gene structures, serum, and tissue concentrations. *Endocr Rev.* 10(1):68-91.
Stewart CE, Rotwein P. 1996. Growth, differentiation, and survival: multiple physiological functions for insulin-like growth factors. *Physiol Rev.* Oct. 1996;76(4):1005-26.
Yakar S, Wu Y, Setser J, Rosen CJ. 2002. The role of circulating IGF-I: lessons from human and animal models. Endocrine. 19(3):239-48.
Shackney SE, McCormack GW, Cuchural GJ Jr. 1978. Growth rate patterns of solid tumors and their relation to responsiveness to therapy: an analytical review. *Ann. Intern. Med.* 89:107-21.
Poznansky MJ, Singh R, Singh B, Fantus G. 1984. Insulin: carrier potential for enzyme and drug therapy. *Science* 223(4642):1304-6.
Bures L, Bostik J, Motycka K, Spundova M, Rehak L. 1988. The use of protein as a carrier of methotrexate for experimental cancer chemotherapy. III. Human serum albumin-methotrexate derivative, its preparation and basic testing. *Neoplasma* 35:329-42.
Ciftci K, Su J, Trovitch PB. 2003. Growth factors and chemotherapeutic modulation of breast cancer cells. *J Pharm Pharmacol* 55(8):1135-41.
Francis GL, Ross M, Ballard FJ, Milner SJ, Senn C, McNeil KA, Wallace JC, King R, Wells JR. 1992. Novel recombinant fusion protein analogues of insulin-like growth factor (IGF)-I indicate the relative importance of IGF-binding protein and receptor binding for enhanced biological potency. *J Mol. Endocrinol.* 8(3):213-23.

(Continued)

*Primary Examiner*—Larry R. Helms
*Assistant Examiner*—Lei Yao
(74) *Attorney, Agent, or Firm*—Hugh McTavish

(57) ABSTRACT

The present invention provides a method of treating cancer involving administering an insulin-like growth factor-1 receptor (IGF-1 receptor) agonist and an anti-cancer chemotherapeutic agent. Also provided are compounds for treating cancer comprising an IGF-1-receptor ligand coupled to an anti-cancer chemotherapeutic agent. Also provided are compounds for treating cancer comprising an insulin-receptor ligand coupled to an anti-cancer chemotherapeutic agent.

17 Claims, 6 Drawing Sheets

OTHER PUBLICATIONS

Tomas FM, Knowles SE, Chandler CS, Francis GL, Owens PC, Ballard FJ. 1993. Anabolic effects of insulin-like growth factor-I (IGF-I) and an IGF-I variant in normal female rats. *J Endocrinol.* 137(3):413-21.

Stehle G, Sinn H, Wunder A, Schrenk HH, Schutt S, Maier-Borst W, Heene DL. 1997. The loading rate determines tumor targeting properties of methotrexate-albumin conjugates in rats. *Anticancer Drugs* 8(7):677-85.

McTavish et al., Novel insulin-like growth factor-methotrexate covalent conjugate inhibits tumor growth . . . Translational Research (2009) 153:275-282.

* cited by examiner

SEQUENCE LISTING

<160> NUMBER OF SEQ ID NOS: 10

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

```
Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 2
<211> LENGTH: 67
<212> TYPE: PRT
<213> ORGANISM: Homo sapiens

<400> SEQUENCE: 2

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65
```

<210> SEQ ID NO 3
<211> LENGTH: 27
<212> TYPE: PRT
<213> ORGANISM: Artificial
<220> FEATURE:
<223> OTHER INFORMATION: Synthetic peptide IGF-1R antagonist

<400> SEQUENCE: 3

```
Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25
```

<210> SEQ ID NO 4
<211> LENGTH: 83
<212> TYPE: PRT
<213> ORGANISM: artificial
<220> FEATURE:
<223> OTHER INFORMATION: LONG-R3-IGF-1, a variant IGF-1 with reduced
      affinity for soluble IGF-1 binding proteins.

<400> SEQUENCE: 4

```
Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala
```

<210> SEQ ID NO 5
<211> LENGTH: 4
<212> TYPE: PRT
<213> ORGANISM: artificial

```
<220> FEATURE:
<223> OTHER INFORMATION: linker peptide

<400> SEQUENCE: 5

Ala Leu Ala Leu
1

<210> SEQ ID NO 6
<211> LENGTH: 54
<212> TYPE: PRT
<213> ORGANISM: Homo sapiens

<400> SEQUENCE: 6

Val Cys Gly Asp Arg Gly Phe Tyr Phe Asn Lys Pro Thr Gly Tyr Gly
1               5                   10                  15

Ser Ser Ser Arg Arg Ala Pro Gln Thr Gly Ile Val Asp Glu Cys Cys
            20                  25                  30

Phe Arg Ser Cys Asp Leu Arg Arg Leu Glu Met Tyr Cys Ala Pro Leu
        35                  40                  45

Lys Pro Ala Lys Ser Ala
    50

<210> SEQ ID NO 7
<211> LENGTH: 83
<212> TYPE: PRT
<213> ORGANISM: Artificial
<220> FEATURE:
<223> OTHER INFORMATION: Met-GH(11)-Val-Asn-IGF-1

<400> SEQUENCE: 7

Met Phe Pro Ala Met Pro Leu Ser Ser Leu Phe Val Asn Gly Pro Glu
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala

<210> SEQ ID NO 8
<211> LENGTH: 83
<212> TYPE: PRT
<213> ORGANISM: Artificial
<220> FEATURE:
<223> OTHER INFORMATION: Met-GH(11)-Val-Asn-[Gly3]-IGF-1

<400> SEQUENCE: 8

Met Phe Pro Ala Met Pro Leu Ser Ser Leu Phe Val Asn Gly Pro Gly
1               5                   10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60
```

```
                                    -continued

Cys Asp Leu Arg Arg Leu Glu Met Tyr Cys Ala Pro Leu Lys Pro Ala
 65                  70                  75                  80

Lys Ser Ala

<210> SEQ ID NO 9
<211> LENGTH: 70
<212> TYPE: PRT
<213> ORGANISM: Artificial
<220> FEATURE:
<223> OTHER INFORMATION: [Arg3]-IGF-1

<400> SEQUENCE: 9

Gly Pro Arg Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
                 20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Met Tyr Cys Ala Pro Leu
 50                  55                  60

Lys Pro Ala Lys Ser Ala
 65                  70

<210> SEQ ID NO 10
<211> LENGTH: 67
<212> TYPE: PRT
<213> ORGANISM: Artificial
<220> FEATURE:
<223> OTHER INFORMATION: des(1-3)IGF-1

<400> SEQUENCE: 10

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Arg Arg Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala
 65
```

COMPOUNDS AND METHODS FOR TREATING CANCER

This application claims priority as a continuation-in-part application under 35 U.S.C. §120 from international application no. PCT/US2004/034704, filed Oct. 21, 2004 and U.S. provisional patent application Ser. No. 60/513,048, filed Oct. 21, 2003, both of which are incorporated by reference.

BACKGROUND

Currently 1.3 million people are diagnosed with cancer each year in the United States alone, and over 500,000 die. Treatment for most types of cancers includes chemotherapy. Chemotherapy drugs are administered systemically and attack all cells of the body, particularly dividing cells, not just cancer cells. Thus, side effects from chemotherapy drugs are often severe. These include anemia, nausea, hair loss, and immune suppression, including neutropenia, due to depletion of white blood cells. The side effects often limit the dose of chemotherapy agents that can be administered.

Cancer cells are obligately glycolytic. That is, they must consume glucose for their energy needs; and they consume it anaerobically, which yields less energy than aerobic respiration. As a consequence, cancer cells must consume a large amount of glucose. Perhaps to assist with acquiring glucose, cancer cells from many types of cancer have been observed to have more insulin receptors than normal cells. (Ayre, S. G., et al., 2000, *Medical Hypotheses* 55:330; Abita, J. F., et al., 1984, *Leukemia Res.* 8:213.) Recently, a method of cancer treatment termed insulin potentiation therapy (IPT) that attempts to exploit the insulin receptors of cancer cells has been introduced in the United States. (Ayre, S. G., et al., 2000, *Medical Hypotheses* 55:330.) The method involves administering insulin to cancer patients, followed a short time later by administering chemotherapy drugs. Lower doses of chemotherapy drugs are used, which reduces the side effects. It is purported that the insulin somehow potentiates the effect of the chemotherapeutic agents on the cancer cells, allowing the use of lower doses.

In vitro data is reported to show that when methotrexate is administered with insulin to breast cancer cells in tissue culture, the same percent cell killing is achieved with $10^4$ lower methotrexate concentrations than when methotrexate is administered alone. (Alabaster, O., et al., 1981, *Eur J. Cancer Clin. Oncol.* 17:1223.) Methotrexate is a folic acid analogue that leads to the depletion of tetrahydrofolate. This interferes with thymidine and purine synthesis, and hence DNA synthesis.

Insulin does not greatly stimulate uptake of chemotherapeutic agents. One study has shown only a 2-fold stimulation of uptake of elipticine by MDA-MB-231 breast cancer cells when the cells were incubated with insulin. (Oster, J. B., et al., 1981, *Eur J. Cancer Clin. Oncol.* 17:1097.) Another study showed a 50% stimulation of uptake of methotrexate by breast cancer cells when the cells were incubated with insulin. (Shilsky, R. L., et al., 1981, *Biochem. Pharmacol.* 30:1537.) Thus, the mechanism for insulin potentiation of methotrexate cytotoxicity must be primarily due to factors other than enhanced uptake.

Another receptor often found in greater numbers in cancer cells than in normal cells of the same tissue type is the insulin-type growth factor-1 receptor (IGF-1 receptor or IGF-1R). IGF-1 is a peptide of 70 amino acid residues having 40% identity with proinsulin. (Daughaday, W. H., et al., 1989, *Endocrine Revs.* 10:68.) Insulin and IGF-1 have some cross-reactivity with each other's receptor. (Soos, M. A., et al., 1993, *Biochem. J.* 290:419.) IGF-1 is secreted by the liver into the circulatory system and stimulates growth of many cell types. IGF-1 is also produced by many cell types throughout the body, including many cancers, for autocrine and paracrine effects. IGF-1 production is stimulated by growth hormone. (Stewart, C. H., e t al., 1996, *Physiol. Revs.* 76:1005; Yakar, S., et al., 2002, *Endocrine* 19:239.)

New methods to enhance the effectiveness of chemotherapy and/or to reduce the side effects of chemotherapy, for instance by reducing the doses of chemotherapeutic agents used, are needed. In addition new anti-cancer chemotherapeutic agents are needed. Preferably the new agents would have lower side effects and/or be more effective in killing cancer cells than agents currently in use.

SUMMARY

Insulin has been shown in vitro to potentiate the effect of one chemotherapeutic agent against breast cancer cells, allowing killing of the cells with lower concentration of methotrexate. This effect presumably depends on the cancer cells having insulin receptors. Most likely the enhancement of killing is because insulin stimulates cells to divide, and methotrexate, like most other chemotherapeutic agents, is more toxic to dividing cells than non-dividing cells. It is known, for instance, that rapidly growing tumors are more sensitive to chemotherapy than slow-growing ones. (Shackney, S. E., et al., 1978, *Ann. Intern. Med.* 89:107.) However, insulin and methotrexate were administered separately, and the insulin had little effect on increasing the uptake of methotrexate by cancer cells.

By physically coupling chemotherapeutic agents to insulin or an insulin receptor ligand, the uptake of the chemotherapeutic agents by the cancer cells is increased. The coupled compounds bind to insulin receptors on the cell surface, thus holding the chemotherapeutic agents on the cell surface, where their uptake is greatly increased relative to the uptake of a chemotherapeutic agent not coupled to insulin. The conjugates and the receptors to which they bind are efficiently taken into the cell by receptor-mediated endocytosis. (Schlessinger, J., et al., 1978, *Proc. Nat'l Acad. Sci. USA* 75:2659; Pilch, P. F., et al., 1983, *J. Cell Biol.* 93:133; (Pozansky, M. J., et al., 1984, *Science* 223:1304.) The chemotherapeutic agent will also be internalized and will be effective against the cancer cells. This is evidenced by the showing that a methotrexate-albumin conjugate is more effective than free methotrexate in treating a cancer implanted in mice. (Bures, L., et al., 1988, *Neoplasma* 35:329.) Because of the enhanced uptake into cancer cells, the compounds containing insulin coupled to a chemotherapeutic agent kill cancer cells more efficiently than free chemotherapeutic agent, even when the free agent is administered in conjunction with insulin.

Uptake of the coupled chemotherapeutic agents into normal cells, however, is not increased as much, because normal cells have fewer insulin receptors than neoplastic cells. Thus, the conjugate gives good selectivity for cancer cells.

Insulin-chemotherapeutic agent conjugates also have the advantage of stimulating cancer cells to divide, thus making them more sensitive to the chemotherapeutic agents, which target dividing cells.

IGF-1 receptors are also overexpressed in most cancer cells. Furthermore, IGF-1 stimulates cancer cells to divide to an even greater extent than insulin. (Stewart, C. H., et al., 1996, *Physiol. Revs.* 76:1005; Yakar, S., et al., 2002, *Endocrine* 19:239.) IGF-1 and insulin also cross-react to some degree with each other's receptors. Since chemotherapeutic drugs generally act against dividing cells, stimulating cancer cells to divide makes them more sensitive to chemotherapeutic agents.

Thus, coadministering IGF-1 with chemotherapeutic agents potentiates the effect of the chemotherapeutic agents by stimulating cancer cells to divide, thus making them more sensitive to chemotherapeutic agents that kill dividing cells. Furthermore, like insulin, IGF-1 can be coupled to chemotherapeutic agents so as to increase uptake of the chemotherapeutic agents into cancer cells, while having less effect on uptake into normal cells, which usually have fewer IGF-1 receptors.

Accordingly, the invention provides a compound for treating cancer comprising an anti-cancer chemotherapeutic agent linked to an insulin receptor ligand, wherein the chemotherapeutic agent is not methotrexate.

Another embodiment of the invention provides a pharmaceutical composition comprising: a compound comprising an anti-cancer chemotherapeutic agent linked to an insulin receptor ligand, wherein the chemotherapeutic agent is not methotrexate. The pharmaceutical composition typically also includes a pharmaceutically acceptable diluent.

Another embodiment of the invention provides a method of treating cancer in a mammal, comprising: administering a compound containing an anti-cancer chemotherapeutic agent linked to an insulin receptor ligand, wherein the compound inhibits growth of the cancer in the mammal.

Another embodiment of the invention provides a method of inhibiting growth of cancer cells comprising: contacting the cancer cells with a compound containing an anti-cancer chemotherapeutic agent linked to an insulin receptor ligand, wherein the compound inhibits the growth of the cancer cells, wherein the chemotherapeutic agent is not methotrexate.

Another embodiment of the invention provides a method of screening a compound for anti-cancer activity comprising: contacting a compound containing a chemotherapeutic agent linked to an insulin receptor ligand with cancer cells; and determining whether the compound inhibits growth of the cancer cells, wherein the chemotherapeutic agent is not methotrexate.

Another embodiment of the invention provides a compound for treating cancer comprising: an anti-cancer chemotherapeutic agent linked to an insulin-like growth factor-1 (IGF-1) receptor ligand, wherein the IGF-1 receptor ligand is not insulin. Preferably, the ligand has a binding affinity for the IGF-1 receptor greater than the binding affinity of insulin for the IGF-1 receptor. Preferably the IGF-1 receptor ligand has a binding affinity for the IGF-1 receptor greater than for the insulin receptor.

Another embodiment of the invention provides a pharmaceutical composition comprising: a compound comprising an anti-cancer chemotherapeutic agent linked to an insulin-like growth factor-1 (IGF-1) receptor ligand; wherein the IGF-1 receptor ligand is not insulin. The pharmaceutical composition typically also includes a pharmaceutically acceptable diluent.

Another embodiment of the invention provides a method of treating cancer in a mammal comprising: administering a compound containing an anti-cancer chemotherapeutic agent linked to an IGF-1 receptor ligand, wherein the compound inhibits growth of the cancer in the mammal, wherein the IGF-1 receptor ligand is not insulin.

Another embodiment of the invention provides a method of inhibiting the growth of cancer cells comprising contacting the cancer cells with a compound comprising an anti-cancer chemotherapeutic agent linked to an IGF-1 receptor ligand, wherein the compound inhibits the growth of the cancer cells, wherein the IGF-1 receptor ligand is not insulin.

Another embodiment of the invention provides a method of screening a compound for anti-cancer activity comprising: contacting cancer cells with a compound containing an anti-cancer chemotherapeutic agent linked to an IGF-1 receptor ligand; and determining whether the compound inhibits growth of the cancer cells, wherein the IGF-1 receptor ligand is not insulin.

Another embodiment of the invention provides a method of treating cancer in a mammal, comprising: administering to the mammal an anti-cancer chemotherapeutic agent and an IGF-1 receptor agonist, wherein the IGF-1 receptor agonist is not insulin.

Another embodiment of the invention provides a method of inhibiting growth of cancer cells comprising: contacting the cells with an anti-cancer chemotherapeutic agent and an IGF-1 receptor agonist; wherein the IGF-1 receptor agonist is not insulin, and wherein the anti-cancer chemotherapeutic agent is not doxorubicin.

DETAILED DESCRIPTION

Figure 1:
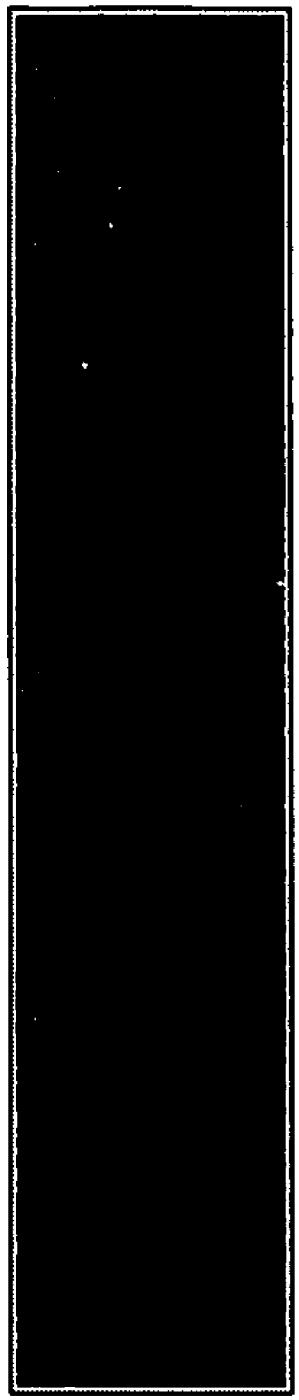
FIG. 1 shows an SDS-PAGE analysis of the conjugate insulin-methotrexate-A.

Definitions:

The term "anti-cancer chemotherapeutic agent" refers to a synthetic, biological, or semi-synthetic compound that is not an enzyme and that kills cancer cells or inhibits the growth of cancer cells while having less effect on non-cancerous cells.

The term "treating cancer" includes, e.g., preventing metastasis, inhibiting growth of a cancer, stopping the growth of cancer, or killing cells of a cancer.

The term "binding affinity" of a ligand for a particular receptor refers to the association constant $K_A$ (the inverse of the dissociation constant $K_D$) or to experimentally determined approximations thereof.

The term "anti-metabolite" refers to an anti-cancer chemotherapeutic agent that bears a structural similarity to a naturally occurring substance, interacts with enzymes as an inhibitor or a substrate, and interferes with cellular processes. Examples include methotrexate, fluorouracil, floxuridine, fludarabine, mercaptopurine, thioguanine, cytarabine, azacytidine, cladribine, and pentostatin.

The term "agonist" refers to a ligand to the insulin receptor or IGF-1 receptor that, when it binds to the receptor, activates the normal biochemical and physiological events triggered by binding of the natural ligand for the receptor (i.e, insulin for the insulin receptor or IGF-1 for the IGF-1 receptor). In particular embodiments, an agonist has at least 20%, at least 30%, or at least 50% of the biological activity of the natural ligand. The activity of an insulin receptor ligand can be measured, for instance, by measuring the hypoglycemic effect (Poznansky, M. J., et al., 1984, *Science* 223:1304). The activity of an insulin-receptor ligand or IGF-1-receptor ligand can be measured in vitro by the measuring the extent of autophosphorylation of the receptor in response to ligand binding, as described in Satyamarthy, K., et al., 2001, *Cancer Res.* 61:7318. MAP kinase phosphorylation can also be measured for the IGF-1 receptor (Satyamarthy, K., et al., 2001, *Cancer Res.* 61:7318).

The term "antagonist" refers to a ligand that has little or no stimulating activity when it binds to the receptor and that competes with or inhibits binding of the natural ligand to the receptor. In particular embodiments, an antagonist has less than 20%, less than 10%, or less than 5% of the activity of the natural ligand (insulin for the insulin receptor or IGF-1 for the IGF-1 receptor).

The "IGF-1 receptor" is also known in the literature as the type 1 IGF receptor.

"Containing" as used herein is open-ended; i.e, it allows the inclusion of other unnamed elements and has the same meaning as "comprising."

Description:

The invention provides a conjugate compound for treating cancer comprising: an anti-cancer chemotherapeutic agent linked to an insulin receptor ligand. In particular embodiments, the anti-cancer chemotherapeutic agent is not methotrexate.

In particular embodiments, the insulin receptor ligand contains or is insulin, IGF-1, or IGF-2. For instance, the insulin receptor ligand can be a monomer of insulin, IGF-1, or IGF-2, or a polymer of insulin, IGF-1, or IGF-2 monomers. In other particular embodiments, the insulin receptor ligand is or contains an antibody, e.g. a monoclonal antibody or a polyclonal antibody.

In a specific embodiment, the insulin receptor ligand is not IGF-1.

Preferably the insulin receptor ligand has a higher binding affinity for the insulin receptor than IGF-1. Preferably the insulin receptor ligand has a higher binding affinity for the insulin receptor than it does for the IGF-1 receptor.

The insulin receptor ligand can be an insulin receptor agonist or insulin receptor antagonist. An agonist has the advantage that it stimulates the cells to divide, thus making them more sensitive to chemotherapeutic agents. However, an antagonist can also be advantageous. Inactivation of the IGF-1 receptor has been shown to promote apoptosis. It is likely that inactivation of the insulin receptor would have the same effect.

Examples of natural agonists of the insulin receptor are insulin, IGF-1, and IGF-2. Methods of identifying antagonist and agonist peptides for the insulin receptor are disclosed in U.S. published patent application 2004/0023887. Some examples of antagonist and agonist peptides are also disclosed.

Any suitable anti-cancer chemotherapeutic agent can be used in the conjugates of the invention and in the methods of treating cancer or inhibiting cancer cell growth by administering the agent and an IGF-1 receptor agonist. For instance, in particular embodiments, the chemotherapeutic agent is mechlorethamine, cyclophosphamide, ifosfamide, melphalan, chlorambucil, thiotepa, hexamethylmelamine, busulfan, carmustine, lomustine, semustine, streptozocin, decarbazine, vincristine, vinblastine, etoposide, teniposide, paclitaxel, docetaxel, daunorubicin, idarubicin, doxorubicin, epirubicin, dactinomycin, plicamycin, mitomycin C, bleomycin, mitoxantrone, fluorouracil, floxuridine, fludarabine, mercaptopurine, thioguanine, cytarabine, azacytidine, cladribine, pentostatin, cisplatin, carboplatin, mitotane, procarbazine, or amsacrine.

In other particular embodiments, the chemotherapeutic agent is mechlorethamine, cyclophosphamide, ifosfamide, melphalan, chlorambucil, thiotepa, hexamethylmelamine, busulfan, carmustine, lomustine, semustine, streptozocin, decarbazine, vincristine, vinblastine, etoposide, teniposide, paclitaxel, docetaxel, daunorubicin, idarubicin, doxorubicin, epirubicin, dactinomycin, plicamycin, mitomycin C, bleomycin, mitoxantrone, methotrexate, fluorouracil, floxuridine, fludarabine, mercaptopurine, thioguanine, cytarabine, azacytidine, cladribine, or pentostatin.

In other particular embodiments, the anti-cancer chemotherapeutic agent is amsacrine, azacytidine, bleomycin, busulfan, capecitabine, carboplatin, carmustine, chlorambucil, cisplatin, cladribine, cyclophosphamide, cytarabine, dactinomycin, daunorubicin, decarbazine, docetaxel, doxorubicin, epirubicin, estramustine, etoposide, floxuridine, fludarabine, fluorouracil, gemcitabine, hexamethylmelamine, idarubicin, ifosfamide, irinotecan, lomustine, mechlorethamine, melphalan, mercaptopurine, methotrexate, mitomycin C, mitotane, mitoxantrone, oxaliplatin, paclitaxel, pemetrexed, pentostatin, plicamycin, procarbazine, ralitrexed, semustine; streptozocin, temozolamide, teniposide, thioguanine, thiotepa, topotecan, trimitrexate, valrubicin, vincristine, vinblastine, vindestine, or vinorelbine.

In particular embodiments, the anti-cancer chemotherapeutic agent is an antimetabolite. For instance, it can be methotrexate, fluorouracil, floxuridine, fludarabine, mercaptopurine, thioguanine, cytarabine, azacytidine, cladribine, pentostatin, pemetrexed, raltitrexed, trimetrexate, capecitabine, or gemcitabine.

In particular embodiments, the anti-cancer chemotherapeutic agent is methotrexate.

In other particular embodiments, the anti-cancer chemotherapeutic agent is an alkylating agent, e.g., mechlorethamine, cyclophosphamide, ifosfamide, melphalan, chlorambucil, thiotepa, hexamethylmelamine, busulfan, carmustine, lomustine, semustine, streptozocin, decarbazine, estramustine, streptozocin, decarbazine, or temozolamide.

In particular embodiments, the anti-cancer chemotherapeutic agent is an antibiotic, e.g., bleomycin, dactinomycin, daunorubicin, doxorubicin, epirubicin, idarubicin, mitomycin, mitoxantrone, or valrubicrin.

In particular embodiments, the anti-cancer chemotherapeutic agent is doxorubicin.

In particular embodiments, the anti-cancer chemotherapeutic agent is docetaxel, paclitaxel, vinblastine, vincristine, vindesine, vinorelbine, irinotecan, topotecan, etoposide, or teniposide.

In particular embodiments, the anti-cancer chemotherapeutic agent has greater activity against cells in S phase of the cell cycle, than in other phases. In other embodiments, the agent has greater activity against cells in G2 phase. In other embodiments, the agent has greater activity against cells in M phase. These agents are particularly suitable, because IGF-1 has been shown to increase the proportion of cells S phase, G2 phase, and M phase. (Ciftci, K., et al., 2003, *J Pharmacy and Pharmacology* 55:1135.) Insulin and other insulin receptor agonists are believed to have the same effect.

In particular embodiments, the anti-cancer chemotherapeutic agent is linked to the insulin receptor ligand or IGF-1 receptor ligand by a hydrolyzable linkage, e.g., a linkage that comprises a Schiff base or imidoamide bond. In other particular embodiments, the hydrolyzable linkage comprises an amide, phosphoester, sulfoester, ester, or glycoside bond.

In some embodiments, the anti-cancer chemotherapeutic agent is linked to the insulin receptor ligand or IGF-1 receptor ligand by a direct bond, e.g, an amide bond between an amine group of the insulin receptor ligand and a carboxyl of the chemotherapeutic agent, or vice versa. In other embodiments the anti-cancer chemotherapeutic agent is linked to the insulin receptor ligand by a linker moiety.

In specific embodiments, the linker moiety comprises a phosphonyldioxy, sulfonyldioxy, sugar, deoxysugar, or peptide.

In particular embodiments where the insulin-receptor ligand is insulin, the chemotherapeutic agent is linked to insulin through an amino group of insulin. In particular embodiments where the IGF-1 receptor ligand is IGF-1, the chemotherapeutic agent is linked to IGF-1 through an amino group of IGF-1. Likewise, the chemotherapeutic agent can be linked to any protein (e.g., IGF-2) or non-protein ligand that has one or more amino groups through one or more of the amino groups.

In particular embodiments where the insulin-receptor ligand is insulin, the chemotherapeutic agent is linked to insulin through a carboxyl group of insulin. In particular embodiments where the IGF-1 receptor ligand is IGF-1, the chemotherapeutic agent is linked to IGF-1 through a carboxyl group of IGF-1. Likewise, the chemotherapeutic agent can be linked to any protein (e.g., IGF-2) or non-protein ligand that has one or more carboxyl groups through one or more of the carboxyl groups.

In particular embodiments where the insulin receptor ligand or IGF-1 receptor ligand is a protein (e.g., insulin, IGF-1, or IGF-2), the chemotherapeutic agent is linked to the protein through an amino acid side chain of the protein. The amino acid side chain can be, for instance, a lysine side chain. In other particular embodiments, the chemotherapeutic agent is linked to the protein ligand through an amino-terminal alpha-amino group or a carboxyl-terminal alpha-carboxyl group.

In particular embodiments of the conjugates, the ratio of chemotherapeutic agent to insulin receptor ligand or IGF-1 receptor ligand is approximately 1:1 (e.g., between 0.5 and 1.5 to 1). In other embodiments, the ratio of chemotherapeutic agent to insulin receptor ligand or IGF-1 receptor ligand is 2 or more (i.e., on average each ligand molecule has two or more chemotherapeutic molecules conjugated to it).

In particular embodiments of the method of treating cancer, the mammal is a human. In other particular embodiments, the mammal is an experimental animal, such as a mouse.

In particular embodiments of the methods of treating cancer, the cancer is lung cancer (e.g., small cell), prostate cancer, colorectal cancer, breast cancer, pancreatic cancer, leukemia, liver cancer, stomach cancer, ovarian cancer, uterine cancer, testicular cancer, brain cancer, non-Hodgkin's lymphoma, Hodgkin's lymphoma, Ewing's sarcoma, osteosarcoma, neuroblastoma, rhabdomyosarcoma, melanoma, or brain cancer.

The invention also provides a method of inhibiting growth of cancer cells involving: contacting the cancer cells with a compound containing an anti-cancer chemotherapeutic agent linked to an insulin receptor ligand, wherein the compound inhibits the growth of the cancer cells. The invention also provides a method of inhibiting growth of cancer cells involving contacting the cancer cells with a compound containing an anti-cancer chemotherapeutic agent linked to an IGF-1 receptor ligand.

In some embodiments of the methods of inhibiting the growth of cancer cells, the conjugate compound kills at least a portion of the cancer cells.

In specific embodiments of the methods of inhibiting the growth of cancer cells, the contacting can be in vitro or in vivo.

In specific embodiments of the methods of inhibiting the growth of cancer cells, the cancer cells can include lung cancer, prostate cancer, colorectal cancer, breast cancer, pancreatic cancer, leukemia, liver cancer, stomach cancer, ovarian cancer, uterine cancer, testicular cancer, brain cancer, non-Hodgkin's lymphoma, Hodgkin's lymphoma, Ewing's sarcoma, osteosarcoma, neuroblastoma, rhabdomyosarcoma, melanoma, or brain cancer cells.

The method of treating cancer in a mammal and the method of inhibiting growth of cancer cells involving use of a compound comprising an anti-cancer chemotherapeutic agent linked to an insulin receptor ligand normally involve cancers where the cells have insulin receptors. Preferably, the cancer cells are also stimulated to proliferate by insulin or the insulin receptor ligand.

Likewise, the method of treating cancer in a mammal and the method of inhibiting growth of cancer cells involving use of a compound comprising an anti-cancer chemotherapeutic agent linked to an IGF-1 receptor ligand normally involve cancers where the cells have IGF-1 receptors. Preferably, the cancer cells are also stimulated to proliferate by IGF-1 or by the IGF-1 receptor ligand.

In the methods of screening a conjugate compound by contacting the compound with cancer cells and determining whether the compound inhibits the growth of the cancer cells, the contacting can be in vitro or in vivo.

In particular embodiments, the compound kills at least a portion of the cancer cells. In particular embodiments, the screening involves determining whether the compound kills the cancer cells.

The invention provides a conjugate compound for treating cancer comprising: an anti-cancer chemotherapeutic agent linked to an IGF-1 receptor ligand, wherein the IGF-1 receptor ligand is not insulin.

In particular embodiments, the IGF-1 receptor ligand is or contains IGF-1. In other embodiments, it is or contains IGF-2. In some embodiments, the ligand comprises IGF-1 or IGF-2. For instance, the ligand can be an IGF-1 or IGF-2 monomer or a polymer of IGF-1 monomers or IGF-2 monomers.

Preferably, the IGF-1 receptor ligand has a binding affinity for the IGF-1 receptor greater than insulin. Preferably, the IGF-1 receptor ligand has a binding affinity for the IGF-1 receptor greater than for the insulin receptor.

In particular embodiments, the IGF-1 receptor ligand is or contains an antibody, e.g., a monoclonal antibody or a polyclonal antibody.

The IGF-1 receptor ligand can be an IGF-1 receptor agonist or antagonist. An agonist has the advantage that it stimulates the cells to divide, thus making them more sensitive to the anti-cancer chemotherapeutic agent. However, an antagonist can also be advantageous. Inactivation of the IGF-1 receptor has been shown to promote apoptosis, so an antagonist will promote apoptosis.

Examples of agonist and antagonist peptide ligands to the IGF-1 receptor, and methods of identifying agonist and antagonist peptide ligands to the IGF-1 receptor, are disclosed in U.S. published patent applications 2004/0023887 and 2003/0092631. One antagonist is the peptide SFYSCLE-SLVNGPAEKSRGQWDGCRKK (SEQ ID NO:3).

Other examples of IGF-1 receptor agonists include variants of IGF-1 that activate the receptor but have reduced affinity for the soluble IGF-1 binding proteins, such as those disclosed in U.S. Pat. No. 4,876,242. IGF binding proteins are natural serum proteins that bind to IGF-1, holding it in circulation and extending its biological half-life. It may be advantageous for the IGF-1 receptor ligands of this invention, particularly agonists co-administered with chemotherapeutic agents as separate molecules, to have reduced binding to the IGF-1 binding proteins, because that reduced binding would accelerate the release of the agent to bind to the IGF-1 receptors. Thus, in some embodiments, the IGF-1 receptor ligand or agonist has reduced affinity for soluble IGF-1 binding proteins, as compared to native IGF-1.

One preferred variant IGF-1 for use in the methods and conjugates of the invention is LONG-R3-IGF-1 (Francis, G. L., et al. 1992, *J. Mol. Endocrinol.* 8:213-223; Tomas, F. M. et al., 1993, *J. Endocrinol.* 137:413-421).

Preferably, the IGF-1 receptor ligand with reduced affinity for soluble IGF-1 binding proteins has at least 5-fold, more preferably at least 10-fold, more preferably still at least 100-fold lower binding affinity for soluble IGF-1 binding proteins than wild-type IGF-1. Binding affinity for the soluble IGF-1 binding proteins can be measured by a competition binding assay against labeled IGF-1 (e.g., I-125-IGF-1), using a mixture of purified IGF-1 binding proteins or rat L6 myoblast-conditioned medium (a naturally produced mixture of IGF-1 binding proteins), as described in Francis, G. L., et al. (1992, *J. Mol. Endocrinol.* 8:213-223); Szabo, L. et al. (1988, *Biochem. Biophys. Res. Commun.* 151:207-214); and Martin, J. L. et al. (1986, *J. Biol. Chem.* 261:8754-8760). Preferably, the variant IGF-1 has an $IC_{50}$ in a competition binding assay against labeled wild-type IGF-1 for binding to soluble IGF-1 binding proteins in L6 myoblast-conditioned medium of greater than 10 nM, more preferably greater than 100 nM.

Preferably, the variant IGF-1 with reduced affinity for soluble IGF-1 binding proteins has affinity for the IGF-1 receptor that is close to wild-type IGF-1 (e.g., less than 30-fold greater than wild-type IGF-1, more preferably less than 10-fold greater than wild-type IGF-1). In specific embodiments, the variant IGF-1 has an $IC_{50}$ in a competition binding assay against labeled wild-type IGF-1 for binding to IGF-1 receptors (e.g., on MCF-7 cells) of less than 50 nM, more preferably less than 10 nM, more preferably still less than 5 nM, more preferably still less than 3 nM). This assay is described in Ross, M. et al. (1989, *Biochem. J.* 258:267-272) and Francis, G. L., et al. (1992, *J. Mol. Endocrinol.* 8:213-223).

The invention also provides a method of treating cancer in a mammal, comprising: administering to the mammal an anti-cancer chemotherapeutic agent and an IGF-1 receptor agonist, wherein the IGF-1 receptor agonist is not insulin.

In a specific embodiment, the IGF-1 receptor agonist has a binding affinity for the IGF-1 receptor greater than insulin.

Normally the method involves cancers where the cells have IGF-1 receptors. Preferably, the cancer cells are also stimulated to proliferate by IGF-1 or by the IGF-1 receptor agonist.

In a particular embodiment of the method, the chemotherapeutic agent is not doxorubicin.

In a particular embodiment, the chemotherapeutic agent is an anti-metabolite.

In particular embodiments, the chemotherapeutic agent is an antibiotic or a plant derivative.

In a particular embodiment, the mammal is a human. In another particular embodiment, the mammal is a mouse.

In specific embodiments, the chemotherapeutic agent is administered within 12 hours, 6 hours, 3 hours, 2 hours, or 1 hour of administering the IGF-1 receptor agonist. The chemotherapeutic agent can be administered before, at the same time as, or after the IGF-1 receptor agonist. Preferably the chemotherapeutic agent is administered together with (i.e., at approximately the same time as) or after the IGF-1 receptor agonist. Where an agent is most active against cancer cells in a particular phase of the cell cycle, such as S phase, the IGF-1 receptor agonist is preferably administered first. The chemotherapeutic agent is preferably administered later, after a time gap such that the maximum number of cells are in the phase of the cell cycle where they are most sensitive when the chemotherapeutic agent is administered.

In specific embodiments, the cancer is lung cancer, prostate cancer, colorectal cancer, breast cancer, pancreatic cancer, leukemia, liver cancer, stomach cancer, ovarian cancer, uterine cancer, testicular cancer, brain cancer, non-Hodgkin's lymphoma, Hodgkin's lymphoma, Ewing's sarcoma, osteosarcoma, neuroblastoma, rhabdomyosarcoma, melanoma, or brain cancer.

In particular embodiments, the IGF-1 receptor agonist is IGF-1 or contains IGF-1.

In particular embodiments, the chemotherapeutic agent is mechlorethamine, cyclophosphamide, ifosfamide, melphalan, chlorambucil, thiotepa, hexamethylmelamine, busulfan, carmustine, lomustine, semustine, streptozocin, decarbazine, vincristine, vinblastine, etoposide, teniposide, paclitaxel, docetaxel, daunorubicin, idarubicin, doxorubicin, epirubicin, dactinomycin, plicamycin, mitomycin C, bleomycin, mitoxantrone, methotrexate, fluorouracil, floxuridine, fludarabine, mercaptopurine, thioguanine, cytarabine, azacytidine, cladribine, pentostatin, cisplatin, carboplatin, mitotane, procarbazine, or amsacrine.

In particular embodiments, the chemotherapeutic agent is methotrexate. In other embodiments, it is doxorubicin.

In a particular embodiment, the IGF-1 receptor agonist is not an insulin receptor ligand.

In specific embodiments, the IGF-1 receptor agonist has a $K_D$ for the insulin receptor of greater than 0.5 nM, greater than 1 nM, or greater than 2 nM.

The invention also provides a method of inhibiting growth of cancer cells comprising: contacting the cells with an anti-cancer chemotherapeutic agent and an IGF-1 receptor agonist; wherein the IGF-1 receptor agonist is not insulin, and wherein the anti-cancer chemotherapeutic agent is not doxorubicin.

In particular embodiments of the method, the IGF-1 receptor agonist has a binding affinity for the IGF-1 receptor greater than insulin.

In particular embodiments of the method, at least a portion of the cancer cells are killed.

The contacting can be in vitro or in vivo.

The invention also provides a method of treating cancer in a mammal involving administering to the mammal an anti-cancer chemotherapeutic agent and an IGF-1 receptor agonist, wherein the IGF-1 receptor agonist is not insulin.

In particular embodiments of that method, the chemotherapeutic agent is not doxorubicin.

In the method involving administering a chemotherapeutic agent and an IGF-1 receptor agonist, the chemotherapeutic agent and agonist are typically not physically associated. But they may be in some embodiments non-covalently associated, e.g., in nanoparticles.

In particular embodiments of the conjugate compounds and methods of the invention, the insulin receptor ligand has a $K_D$ for the insulin receptor of less than 10 μM, less than 1

μM, less than 100 nM, less than 50 nM, less than 20 nM, less than 10 nM, less than 5 nM, less than 2 nM, or less than 1 nM.

In particular embodiments of the conjugate compounds and methods of the invention, the IGF-1 receptor ligand has a $K_D$ for the IGF-1 receptor of less than less than 10 μM, less than 1 μM, less than 100 nM, less than 50 nM, less than 20 nM, less than 10 nM, less than 5 nM, less than 2 nM, or less than 1 nM.

Guidelines for Coupling Anti-Cancer Chemotherapeutic Agents to Receptor Ligands

The natural ligands to the insulin and IGF-1 receptors are proteins, namely insulin, IGF-1, and IGF-2. Chemotherapeutic agents are typically coupled to proteins through the reactive groups present on proteins. These include the N-terminal alpha-amino group, the C-terminal alpha-carboxyl group, the side-chain amino group of lysine, the side-chain carboxyl groups of aspartic acid and glutamic acid, the side chain thiol of cysteine, and the side chain of arginine. Other reactive side chains found on proteins are the side-chain hydroxyl of serine and threonine, the hydroxyaryl of tyrosine, the imidazole of histidine, and the methionine side chain.

Many of the same reactive groups are found on chemotherapeutic agents and on non-proteinaceous ligands of the insulin and IGF-1 receptors. Thus, many of the principles of modification and cross-linking of proteins discussed herein also apply to modification and cross-linking of chemotherapeutic agents and non-proteinaceous ligands.

The chemistry and principles of protein conjugation and cross-linking are described in Wong, Shan S., *Chemistry of Protein Conjugation and Cross-Linking,* 1991, CRC Press, Boca Raton, Fla. Other sources for information on this chemistry include the Pierce Biochemistry catalog; and Greene, T. W., and Wutz, P. G. M., *Protecting Groups in Organic Synthesis,* second edition 1991, John Wiley & Sons, Inc., New York, and references cited therein.

The strongest nucleophile of amino acid side chains is the thiol of reduced cysteine side chains. The thiol reacts with most protein modifying reagents. Alpha-haloacetamides and maleimides are considered to react specifically with cysteine residues, particularly at pH 7.0 and below. Thiols also react by disulfide interchange with disulfide reagents.

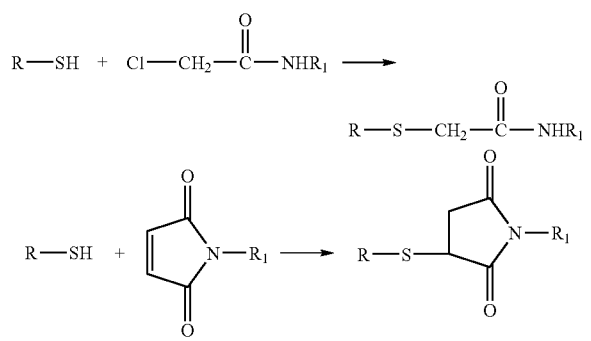

Amino groups are the next-strongest nucleophiles found on proteins. Aldehydes react with amino groups to form Schiff bases. The Schiff bases are hydrolyzable, which can be an advantage in the present invention. With uptake into cancer cells of a ligand-chemotherapeutic agent conjugate, in some cases it is necessary that the chemotherapeutic agent is cleaved from the conjugate for it to be active. This is better accomplished if the chemotherapeutic agent is linked to the ligand by a cleavable linkage, such as a hydrolyzable linkage.

Cleavable linkages can be cleaved spontaneously or by enzymes in the cell. For instance, amide bonds are cleaved by certain enzymes, including proteases. A Schiff base linkage spontaneously hydrolyzes at an appreciable rate. A disulfide linkage is expected to be reductively cleaved in the intracellular reducing environment of a cancer cell.

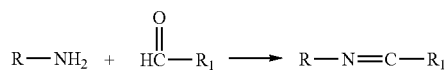

The Schiff base formed by reaction of an amino group with an aldehyde can be stabilized by reduction with, for instance, sodium borohydride or pyridine borane. Pyridine borane has the advantage of not reducing disulfides, which are found in insulin, IGF-1, and IGF-2 and are essential for the structure of those proteins.

Sugars or other moieties having hydroxyl groups on adjacent carbons, which are found in some chemotherapeutic agents, can be modified to react with amino groups by oxidizing the sugars with, for instance, periodate. This cleaves between the carbons and produces a dialdehyde. The aldehyde groups will react with amino groups.

A dialdehyde, such as glutaraldehyde, will cross-link two molecules having amino groups.

Other amino reagents include activated carbonyls, such as N-hydroxysuccinimide esters, p-nitrophenyl esters, or acid anhydrides (e.g., succinic anhydride).

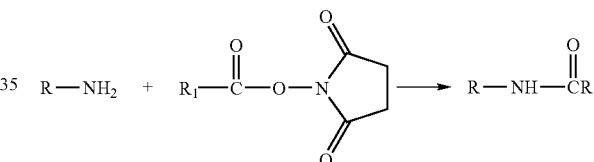

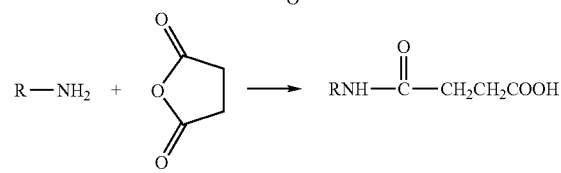

Amino groups also react with sulfonyl halides and aryl halides (e.g, 2,4-dinitrofluorobenzene).

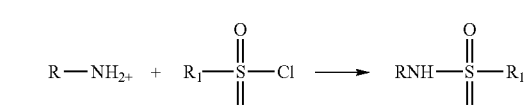

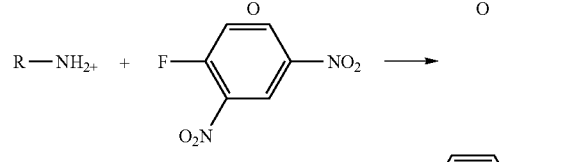

Amino groups also react with isocyanates and isothiocyanates to form urea or thiourea derivatives.

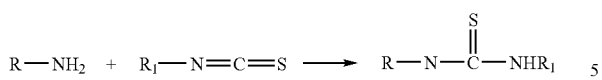

Imidoesters are the most specific acylating agents for amino groups. Imidoesters react specifically with amines to from imidoamides at pHs between about 7 and 10. This reaction has the advantage of maintaining charge stability by generating a positively charged group, the imidoamide, at the former amino group. Imidoamides also slowly hydrolyze at pHs above neutrality, which can also be an advantage in that the hydrolysis can release free chemotherapeutic agent in the cancer cell.

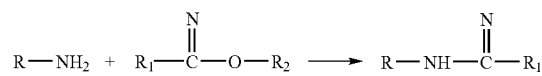

Carboxyl groups react specifically with diazoacetate and diazoacetamide under mild acid conditions, e.g., pH 5.

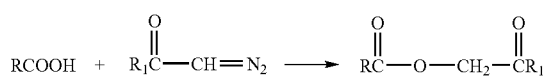

The most important chemical modification of carboxyls uses carbodiimides, such as 1-cyclohexyl-3-(2-morpholinyl-4-ethyl)carbodiimide (CMC) and 3-(3-dimethylaminopropyl)carbodiimide (EDC). In the presence of an amine, carbodiimides form an amide bond to the carboxyl in two steps. In the first step, the carboxyl group adds to the carbodiimide to form an O-acylisourea intermediate. Subsequent reaction with an amine yields the corresponding amide.

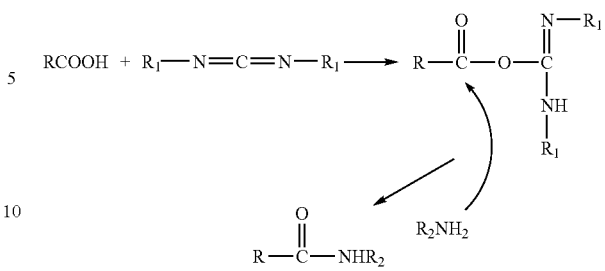

A particularly important carbodiimide reaction is its use in activating carboxyls with N-hydroxysuccinimide to form an N-hydroxysuccinimide ester.

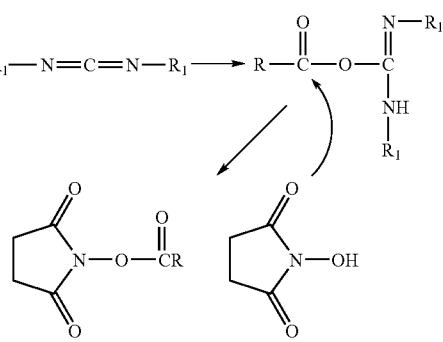

The activated carboxyl is stable enough to be isolated, but will then readily react with amino groups to form an amide bond.

Succinimides such as N-succinimidyl-3-[2-pyridyldithio] propionate (SPDP) can be used to couple two compounds through amino groups. (See Pierce Biotechnology catalog, and Thorpe, P. E. et al. 1982, *Immunol. Rev.* 62:119-158.)

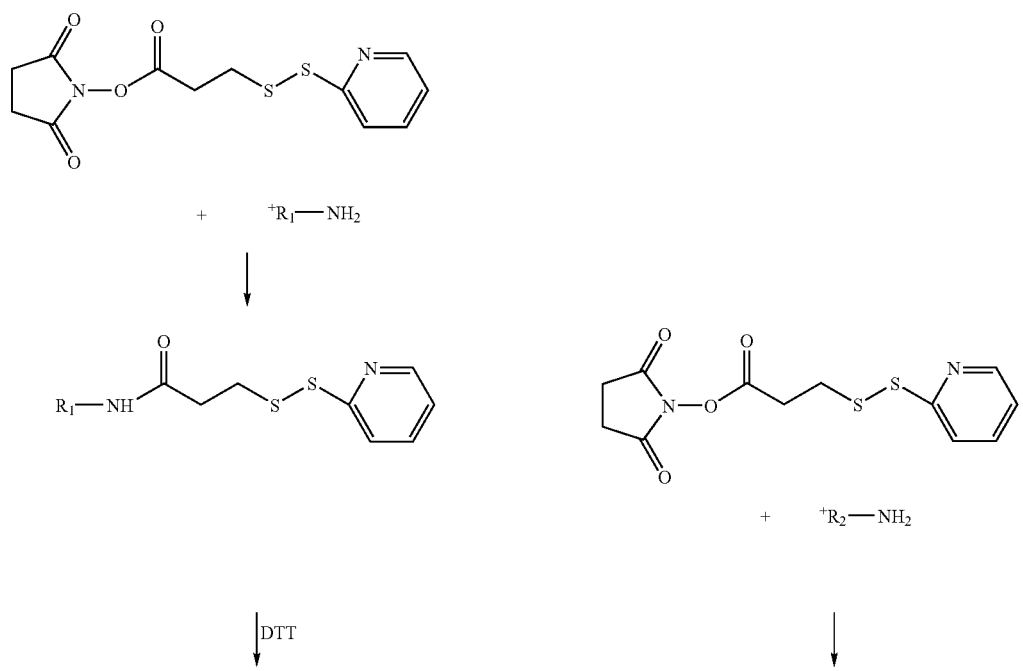

-continued

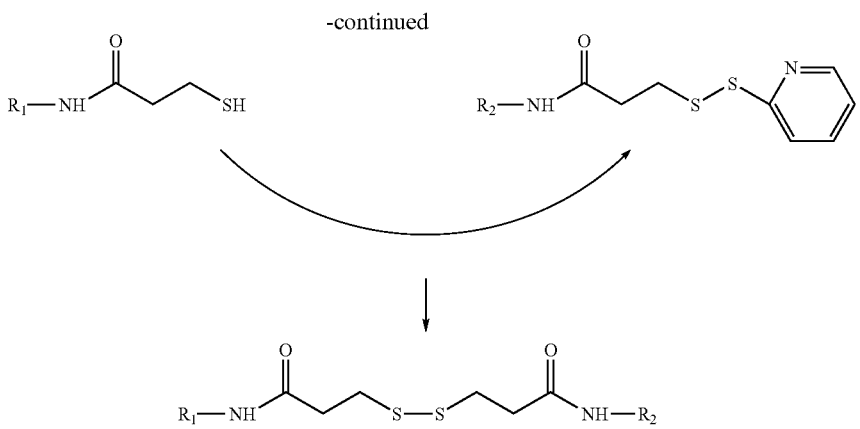

Arginine reacts with vicinal dialdehydes or diketones, such as glyoxal, 2,3-butanedione, and 1,2-cyclohexanedione. Borate may stabilize the adduct, if stabilization is desired.

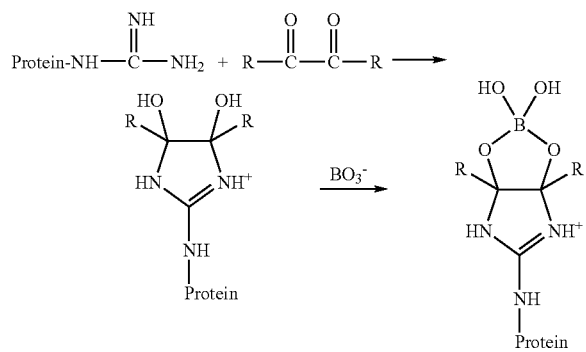

The reactive groups can also be interchanged with other reactive groups by some of the above reactions. For instance, modification of an amino group with an acid anhydride such as succinic anhydride, replaces the positively charged amino group with a free carboxyl group. Likewise, reaction of a carboxyl group with a carbodiimide and a diamine, such as ethylene diamine, replaces the carboxyl group with a free amino group.

Cross-linking: Reagents containing two of the reactive groups described above, for instance two amino-reactive groups or an amino-reactive and a thiol-reactive group, can be used to cross-link a chemotherapeutic agent containing one of the appropriate groups to an insulin or IGF-1 receptor ligand containing the other appropriate group. In addition, a carboxyl (of, e.g., a chemotherapeutic agent) activated with a carbodiimide or a carbodiimide and N-hydroxysuccinimide can react with an amino group (of, e.g., a protein ligand) to form an amide bond cross-link.

Insulin, IGF-1, and IGF-2

The structure of human insulin is shown below.

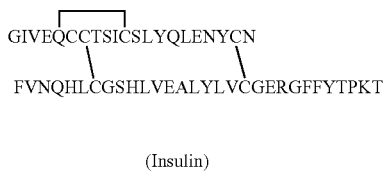

(Insulin)

The sequence of human insulin-like growth factor-1 (IGF-1) is shown below as SEQ ID NO:1.

```
                                          (SEQ ID NO: 1)
GPETLCGAELVDALQFVCGDRGFYFNKPTGYGSSSRRAPQT
GIVDECCFRSCDLRRLEMYCAPLKPAKSA
```

The amino acid sequence of human IGF-2 is shown below as SEQ ID NO:2.

```
                                          (SEQ ID NO: 2)
AYRPSETLCGGELVDTLQFVCGDRGFYFSRPASRVSRRSR
GIVEECCFRSCDLALLETYCATPAKSE
```

The cysteine residues in all three proteins are all in disulfide bridges. Thus, the most nucleophilic free side chains present on the proteins are the lysine amino groups, of which there is one in insulin, three in IGF-1, and one in IGF-2. In addition insulin has two peptides and thus two N-terminal alpha-amino groups, while IGF-1 and IGF-2 have one N-terminal alpha-amino group each. Other reactive side-chains, including carboxyl-containing side chains, histidine side chains, and arginine side chains, are also present on the proteins, as well as the C-terminal alpha-carboxyl groups.

A preferred IGF-1 variant with reduced binding affinity for the soluble IGF-1 binding proteins is LONG-R3-IGF-1 (GroPep Ltd., Australia), which has the sequence

```
                                          (SEQ ID NO: 4)
MFPAMPLSSL FVNGPRTLC GAELVDALQF VCGDRGFYFN
KPTGYGSSSRR APQTGIVDEC CFRSCDLRRL EMYCAPLKPA KSA
```

The invention will now be illustrated by the following examples. The examples are intended to illustrate the invention but not to limit the scope of the invention.

EXAMPLES

Synthetic Example 1

Methotrexate Coupling to Insulin, IGF-1, and IGF-2

Two-step procedure: This procedure is modified from Stehle, G., et al., *Anti-Cancer Drugs* 8:677 (1997) and Bures, L., et al., *Neoplasma* 35:329 (1988). Methotrexate (MTX) is dissolved in water at 20 mg/ml. An NaOH solution can be added dropwise to assist dissolving the MTX free acid. To 1 ml of this MTX solution, 14 mg N,N'-dicyclohexylcarbodiimide (DCC) and 50 mg of N-hydroxysuccinimide are added. The mixture is incubated for 12 hours to form activated MTX, methotrexate-succinimide ester (MTX-SE) (Scheme 1).

If desired, activated MTX-SE can be separated from MTX by thin-layer chromatography, as described in Stehle, G., et al., *Anti-Cancer Drugs* 8:677 (1997). MTX-SE is slowly added to a solution of 5-10 mg/ml insulin in 0.13 M sodium phosphate, pH 7.4. To achieve a loading rate of about 1 mole MTX per mole insulin, approximately 10 mg of MTX-SE is added per 100 mg of insulin. After coupling, the coupled MTX-insulin is separated from unreacted MTX and MTX-SE by separation with SEPHADEX G-25 or G-10 chromatography. This procedure couples MTX predominantly to free primary amine groups. Insulin has three primary amines—one lysine residue with a side chain amine, and two peptides, each with a N-terminal alpha-amino group.

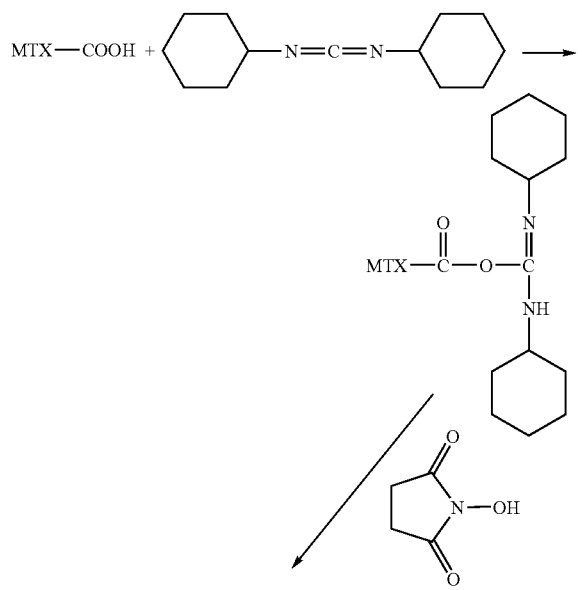

Scheme 1

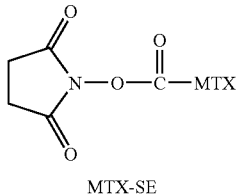

MTX-SE

The amount of unbound MTX in the low molecular weight fractions from the SEPHADEX G-25 or G-10 chromatography can be determined by absorption at 370 nm in sodium bicarbonate buffer, 0.17 M, pH 8.5. By subtraction from the amount of starting MTX-SE added to insulin, the amount of coupled MTX can be calculated.

If desired, the different species of insulin resulting from the coupling can be separated by ion-exchange or hydrophobic exchange FPLC (Pharmacia, Inc.), reverse-phase HPLC, or other techniques known to persons of skill in the art. The different species include unreacted insulin, the species of insulin with one MTX coupled through its terminal carboxyl to one of the three amino groups on insulin, species of insulin with two MTX coupled through their terminal carboxyls to two of the amino groups, and the one species with an MTX coupled through its terminal carboxyl to each of the three amino groups. The three species of insulin with one MTX coupled through its terminal COOH to an amino group of insulin, are shown below.

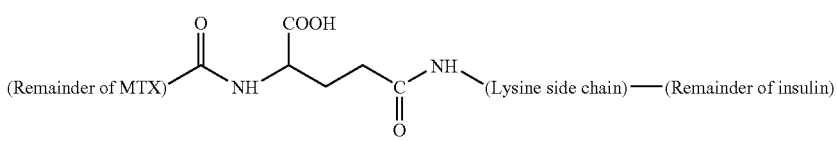

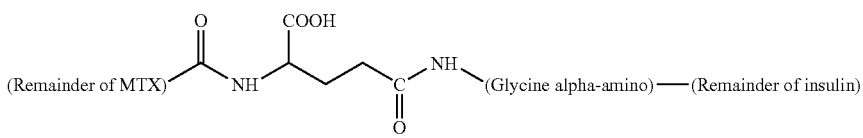

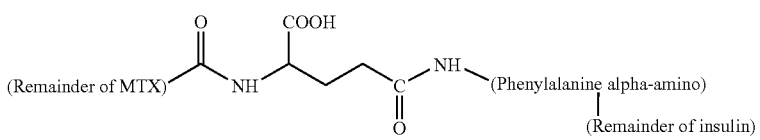

In addition, the MTX-insulin species will include species with MTX coupled through its other carboxyl group to the amino groups of insulin.

One-step procedure: Insulin (100 mg) is dissolved in water (50 ml) and the pH adjusted to 7.2. Ten to fifty mg MTX (free acid) is dissolved in 40 ml water with dropwise addition of a NaOH solution, and the pH adjusted to 7.2. The insulin and MTX solutions are mixed, solid 1-ethyl-3-(3'-dimethylaminopropyl)-carbodiimide methoiodide (EDC) (480 mg) is added, and the solution is stirred for 20 hours. The pH is monitored and maintained at 7.2-7.5 by addition of 0.5 M HCl. After reaction, the mixture is concentrated by ultrafiltration or other methods known to persons of skill in the art, such as lyophilization, water absorption by SEPHADEX G-10, or dialysis against solid sucrose. The concentrated insulin-MTX solution is passed through a SEPHADEX G-10 column to remove unreacted MTX and EDC.

The one-step procedure produces some cross-linking of insulin-MTX monomers by EDC cross-linking of the carboxyl groups of the insulin or MTX of one insulin-MTX monomer with an amino group of the insulin or MTX of another MTX monomer. Insulin-MTX prepared by the two step procedure will not be polymerized, but polymers could be prepared by reacting the insulin-MTX monomers with EDC or DCC. There may be some advantage to polymerizing insulin-MTX because the polymers may bind more tightly to the insulin and IGF-1 receptors.

If it is found that the amino groups of insulin are essential to binding, other reactive groups can be used for coupling. For instance, carboxyl side chains or the C-termini carboxyl groups can be activated with carbodiimide or a carbodiimide and an N-hydroxysuccinimide. The carboxyls of methotrexate can be modified with a carbodiimide and ethylene diamine to append a reactive amino group to MTX. The free amino group of the appended ethylene diamine moiety can then react with the activated carboxyl of insulin to couple MTX to insulin.

Other methods of coupling MTX to insulin will be apparent to persons of skill in the art.

Methotrexate can be coupled to IGF-1 or IGF-2 by the procedures used to couple methotrexate to insulin.

Synthetic Example 2

Doxorubicin Coupling to Insulin, IGF-1, and IGF-2

The structure of doxorubicin is shown below.

The most reactive group on doxorubicin for coupling is the amino group.

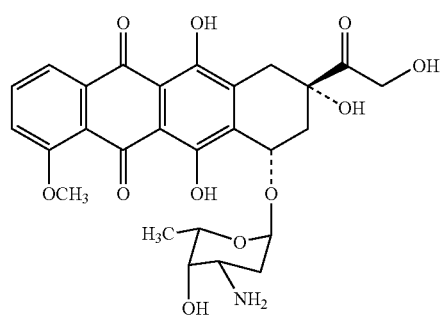

Doxorubicin can be coupled through its amino group to an amino group on insulin by reaction with a di-imidoester, such as dimethyladipimidate-2-HCl (Pierce Biochemical, Inc.), or a disuccinimidyl ester, such as disuccinimidyl glutarate (Pierce Biochemical, Inc.). One of the products generated by coupling with dimethyladipimidate is shown below.

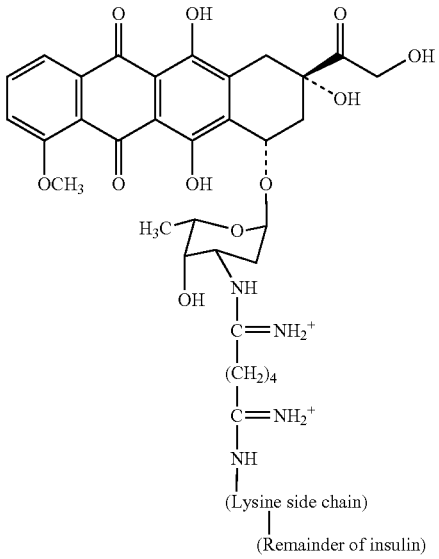

Coupling also occurs with the two terminal alpha-amino groups of insulin.

A solution containing insulin at approximately 3 mg/ml (0.5 mM) and 5 mM doxorubicin is prepared in carbonate buffer, pH 8.8. DMA is added to 5 mM concentration and the solution incubated at room temperature or 37° C. for 15 minutes to 1 hour. The reaction is quenched by the addition of excess Tris buffer. Protein is separated from buffer and unreacted reagents by SEPHADEX G-10 chromatography.

Synthetic Example 3

5-Fluorouracil Coupling to Insulin, IGF-1, and IGF-2

Fluorouracil is coupled to a sugar or deoxysugar, such as 2'-deoxyribose, to form a nucleoside. The sugar portion of the nucleoside is coupled to insulin, IGF-1, and IGF-2. In one embodiment, the starting material is deoxyuridine. Deoxyuridine is fluoridated to form 5-fluorodeoxyuridine. (Robins, M. J., 1976, *J. Am. Chem. Soc.* 98:7381.)

First, the sugar hydroxyls of deoxyuridine are acetylated. To 12 ml of $Ac_2O$, is added 1.03 g 2'-deoxyuridine and 25 mg of 4-N,N-dimethylpyridine. The mixture is allowed to react for 24 hours at room temperature. The solution is then evaporated at 35° C. The residue is coevaporated with three 25 ml portions of ethanol.

Next, the acetylated deoxyuridine is fluoridated at the 5 position. The solid product of the previous step (0.624 g) is dissolved in 15 ml of $CHCl_3$. $CF_3OF$ (0.9 g) is dissolved in 10 ml of $CCl_3F$ at $-78°$ C. The $CF_3OF$ solution is added slowly to the deoxyuridine solution with stirring at $-78°$ C., and the reaction is monitored by following the disappearance of uracil absorption at 260 nm. After minimization of the 260 nm absorption, stirring is continued for 5 minutes. Nitrogen gas is bubbled through the solution to remove excess $CF_3°$ F. The solution is then warmed to room temperature and the solvents evaporated under reduced pressure.

To deacetylate the acetylated fluorodeoxyuridine, the residue of the previous step is stirred in 50 ml MeOH with 6 ml of DOWEX 50-X8($H^+$) resin and filtered. The resin is washed thoroughly with MeOH and the washes recovered. The methanol solvent is evaporated. The residue is coevaporated with EtOH-EtOAc-$PhCH_3$ (1:1:2). The product is crystallized from 20 ml of absolute ethanol.

The product is reacted with a difunctional cross-linker that activates the sugar hydroxyls, primarily the 5' hydroxyl. In one embodiment, fluorodeoxyuridine is reacted with compound 11 in an anhydrous solvent such as chloroform.

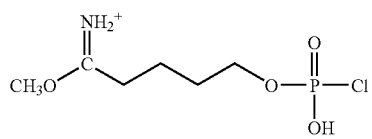

11

This adds compound 11 by the phosphate group to the 5' hydroxyl, resulting in methoxyimidopropyl-FdUMP. (Some reaction with the 3' hydroxyl will also occur.) The imidoester group is then used to cross-link the compound to a protein amino group in aqueous medium to produce the product shown below.

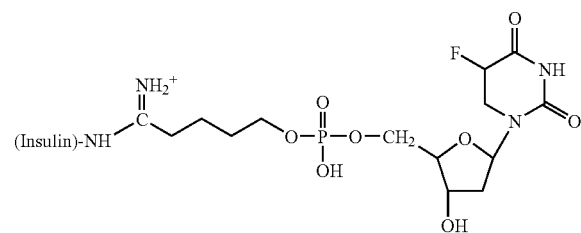

In another embodiment, the fluorodeoxyuridine is activated at elevated pH with a bifunctional cross-linking agent such as disuccinimidyl suberate (DSS) and the activated fluorodeoxyuridine is reacted with a protein to cross-link to an amino group on the protein. DSS (0.5 mM final concentration) is mixed in carbonate buffer at pH 10 with fluorodeoxyuridine (0.5 mM) and reacted for 1 hour at 4° C. The pH is adjusted to about 7-8 in phosphate or HEPES buffer. Insulin, IGF-1, or IGF-2 is added at approximately 0.5 mM and the reaction continued for 30 min. The reaction is quenched by the addition of Tris buffer. The protein is concentrated by ultafiltration and then separated from salts and unreacted reagents by SEPHADEX G-10 chromatography.

Synthetic Example 4

Bleomycin Coupling to Insulin, IGF-1, and IGF-2

The bleomycins have two free primary amino groups and a secondary amine available for coupling to amino groups of insulin, IGF-1, and IGF-2 with cross-linkers such as disuccinimidyl suberate or dimethyladipimidate.

Synthetic Example 5

Vincristine Coupling to Insulin, IGF-1, and IGF-2

Vincristine has one secondary amine available for coupling, and thus can be coupled by bifunctional amine-reactive reagents, such as DSS or DMA to an amino group on insulin, IGF-1, or IGF-2.

Synthetic Example 6

Paclitaxel Coupling to Insulin, IGF-1, and IGF-2

Paclitaxel has no free reactive amino groups and no sulfhydryls, but has two available hydroxyls. The hydroxyls can be activated at elevated pH with a bifunctional coupling agent such as DSS, and the activated paclitaxel can then be reacted with insulin, IGF-1, or IGF-2, resulting in coupling to an amino group on the protein.

Synthetic Example 7

Etoposide Coupling to Insulin, IGF-1, and IGF-2

The phenolic hydroxyl of etoposide will nucleophilically attack a phosphoryl halide to form etoposide phosphate. (U.S. Pat. No. 5,041,424.) An analogous reaction can be used to couple etoposide to insulin, IGF-1, or IGF-2.

Etoposide is dissolved in dry acetonitrile. A bifunctional reagent containing a phosphoryl halide at one end and an amine-reactive agent at the other, such as compound 12 below, is added to react with etoposide. The activated etoposide product is purified and then mixed with protein, where the second functionality of the cross-linker reacts with an amine group of the protein to cross-link etoposide phosphate to the protein.

Alternatively, in a one step procedure, etoposide and protein can be mixed together with a cross-linker such as DMA or DSS. The phenolic hydroxyl of etoposide and an amino group of the protein will react with the two functionalities of the cross-linker to cross-link etoposide and the protein together, as is described for doxorubicin and fluorouracil coupling.

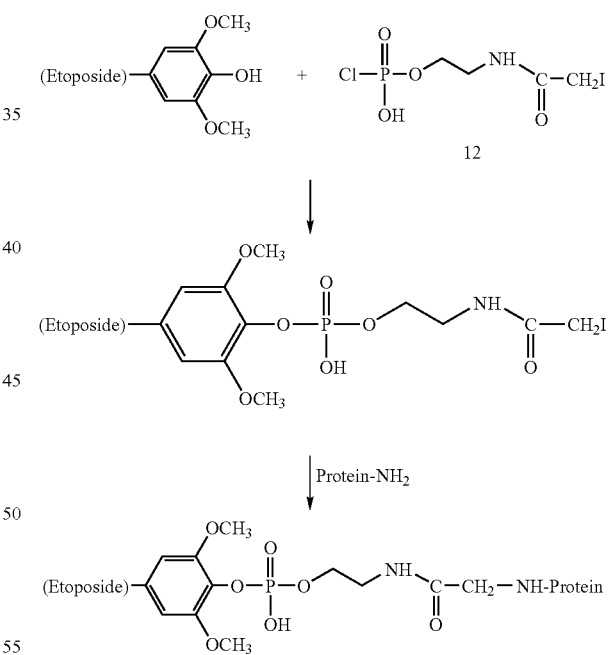

Synthetic Example 8

Cyclophosphamide Coupling to Insulin, IGF-1, and IGF-2

Cyclophosphamide has the structure shown below. It is oxidized in mammals in vivo and decomposes to the active species phophoramide mustard. (Kwon, C.-H., et al., 1991, *J. Med. Chem.* 34:588.)

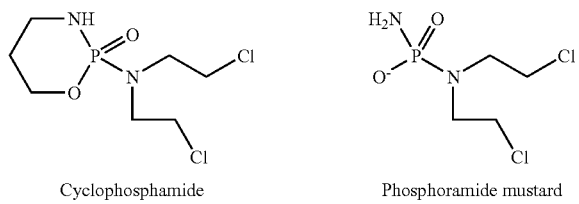

Cyclophosphamide               Phosphoramide mustard

Cyclophosphamide can be coupled, for instance, through a ribose and pyrimidine to an amino group in insulin, IGF-1, or IGF-2. The structure below, bischloroethylphosphoramide-thymidine-amine (BCPTA) is synthesized, and then cross-linked through its free primary amino group to the protein.

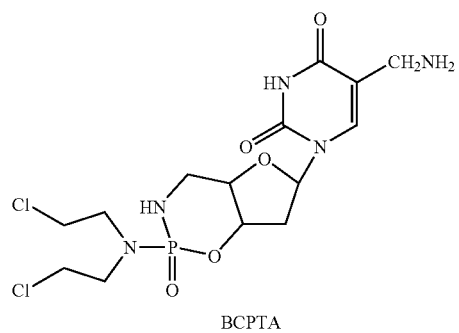

BCPTA

To prepare BCPTA, 5'-amino-2'-deoxy-aminocytidine (13) is synthesized by known chemical procedures.

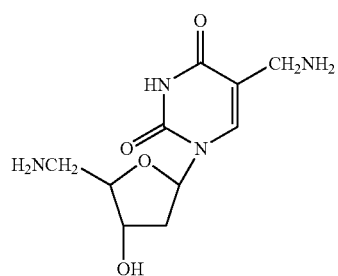

13

A solution of bis(2-chloroethyl)phosphoramidic dichloride (2 mmol) in 5 ml ethyl acetate is added to a stirred mixture of 5'-amino-2'-deoxy-aminocytidine (13) (2 mmol) and triethylamidine (4 mmol) in 15 ml dimethylformamide and stirred at room temperature for 48 hours. (Lin, T.-S., et al., 1980, *J. Med. Chem.* 23:1235.) After isolation of the product bischloroethylphosphoramide-thymidine-amine, the product is cross-linked to amino groups of insulin, IGF-1, or IGF-2 by a difunctional cross-linker such as DMA or DSS as described in synthetic examples 2 and 3.

Example 1

Synthesis and in vitro Testing of Three Methotrexate-Insulin Conjugates

Three insulin-MTX conjugates were synthesized by the one-step procedure of synthetic example 1.

Conjugate Insulin-MTX-A. This conjugate was designed to have approximately 3 MTX attached to each insulin by direct amide bonds to the two alpha amino groups and one lysine side chain of insulin. MTX (20.1 mg) was dissolved in 0.5 ml 20 mM sodium phosphate, pH 7.4, and 77 μl 1M NaOH (NaOH added to neutralize and dissolve the MTX). Insulin (9.1 mg) was dissolved in 0.5 ml 20 mM sodium phosphate, pH 7.4. The insulin and MTX solutions were mixed. EDC (27.3 mg) was dissolved in 20 mM sodium phosphate pH 7.4 and immediately added to the insulin-MTX solution to give a final volume of 1.2 ml. The reaction was allowed to proceed at room temperature for 2 hours. The product mixture was passed through a 10 ml PD-10 column equilibrated with 30 mM glycine-NaOH, pH 10.5, to separate the insulin-MTX conjugate from unreacted MTX and other reagents on the basis of size. The product was analyzed by optical spectroscopy in pH 7.4 buffer to measure the absorbance at 372 nm to quantify methotrexate. Assuming 100% recovery of insulin, and using $\epsilon_{372\,nm}=6.85$ mM$^{-1}$, the molar ratio of methotrexate to insulin was 3.4.

Conjugate Insulin-MTX-B. This involved a conjugate of methotrexate through a peptide linker to insulin. First, methotrexate was conjugated through its terminal carboxyl group to the amino terminus of the tetrapeptide (Ala-Leu-Ala-Leu, SEQ ID NO:5). Peptide (1.8 mg) and MTX (4.6 mg) (a 1:1 molar ratio) were dissolved together in 25 mM sodium phosphate, pH 7.4, in a final volume of 0.5 ml. Solid EDC (4 mg) was added to the solution, and the reaction proceeded for 2 hours at room temperature. A small aliquot of the product was analyzed by thin-layer chromatography on silica plates with 50% acetone, 50% methanol as the mobile phase. The MTX-peptide reaction product migrated slower than unreacted MTX, indicating that the conjugation was successful.

The MTX-peptide product mixture was added to 4.51 mg insulin in a final volume of 0.74 ml 25 mM sodium phosphate pH 7.4. (This has a peptide:insulin molar ratio of 6:1.) EDC (13 mg freshly dissolved in water) was added to the mixture to give a final volume of 0.83 ml. The reaction was allowed to proceed at room temperature for 2 hours. The product mixture was passed through a 10 ml PD-10 column to separate insulin-conjugate product from unreacted smaller reagents. Optical spectroscopy indicated the product has approximately 3 MTX per insulin.

Conjugate Insulin-MTX-C. This conjugate was a conjugate with MTX directly attached to insulin without a linker as in the insulin-MXT-A conjugate, but with only approximately 1 MTX per insulin. Insulin (11.8 mg) and MTX (1.38 mg) (a molar ratio of MTX:insulin of 1.5:1) were dissolved and mixed as described for the synthesis of conjugate Insulin-MTX-A. Freshly dissolved EDC (18 mg) was added to the mixture and the reaction was allowed to proceed at room temperature for 2 hours. The product was found to form a precipitate, which could be dissolved by adding glycine-NaOH buffer (50 mM glycine) and adjusting the pH to 10.5 with NaOH. The solubilized product mixture was passed through a 10 ml PD-10 column to separate the conjugate from unreacted reagents on the basis of size. The purified insulin-MTX conjugate was determined to have approximately 1.0 MTX per insulin by the absorbance at 372 nm.

The three types of conjugates were analyzed by SDS-PAGE. In addition to conjugating methotrexate to insulin, the conjugation procedure can couple insulin molecules together through an amino group of one insulin to a carboxyl group of another to form dimers, trimers, or higher multimers. The multimers may also have methotrexates attached to them. The SDS-PAGE analysis of conjugate insulin-MTX-A is shown in FIG. 1. The majority of product was monomer with some dimer and trimer. Very similar results were found for the conjugates insulin-MTX-B and insulin-MTX-C.

Figure 2:
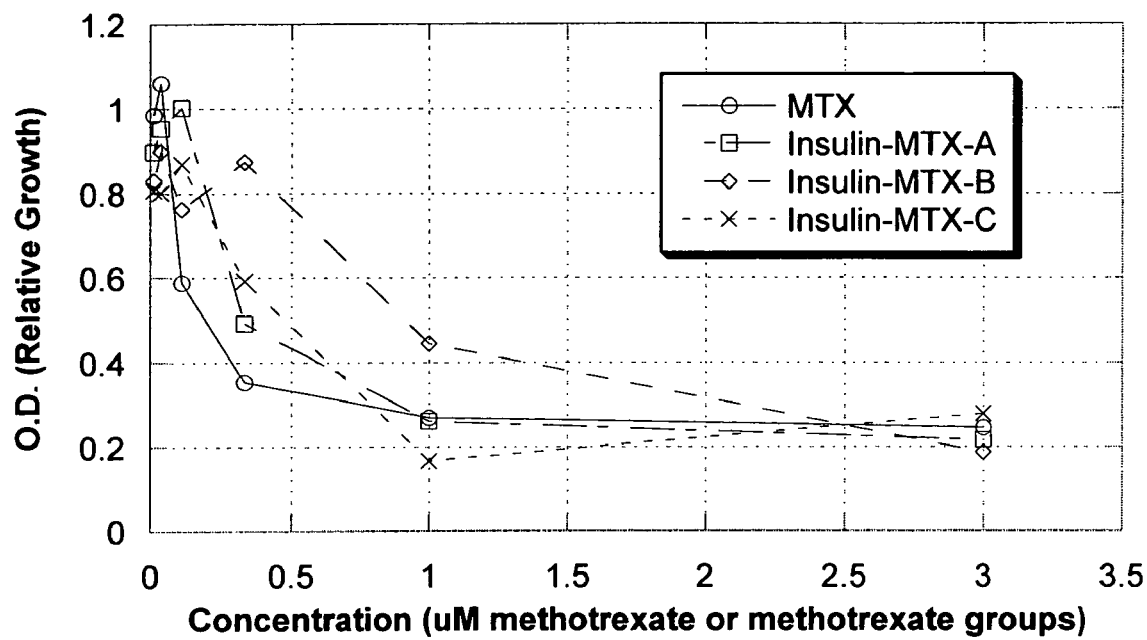
FIG. 2 is a plot showing the concentration dependence of in vitro growth inhibition of FSAII tumor cells by methotrexate and insulin-methotrexate conjugates.

In vitro growth inhibition. The mouse fibrosarcoma cell line FSAII was cultured in RPMI medium supplemented with 10% fetal calf serum (FCS) (rich medium). The cells were grown in a 5% $CO_2$ atmosphere at 37° C. in 100 $cm^2$ plastic tissue culture dishes (20 ml medium). Cells were passed every 4-6 days and seeded at $2 \times 10^6$ cells per plate. Cells were harvested by washing once in Hank's balanced salt solution, and then digesting with 3 ml of trypsin-EDTA for 3-10 minutes until cells had detached. Trypsinization was stopped by adding rich medium. The harvested cells were washed by centrifugation and resuspended in rich medium, and then plated in a 96-well plate at 12,000 cells per well in rich medium. Plates were incubated in the rich medium 16 hours and then transferred to minimal medium (100 µl/well), which lacked serum and thus lacked insulin and IGF and other growth factors. Minimal medium was RPMI supplemented with 10 µg/ml transferrin (iron-loaded) and 200 µg/ml bovine serum albumin. The cells were adapted to minimal medium for 6 hours, and then methotrexate or a test methotrexate conjugate was added at concentrations from 2 nM to 2 µM (methotrexate or methotrexate groups in the conjugates). Each condition was tested in triplicate. After 72 hours incubation at 37° C., cell proliferation was assayed by the cell-counting kit-8, based on tetrazolium dye reduction, similar to the MTT assay (Dojindo Molecular Technologies, Gaithersburg, Md.). The results are shown in FIG. 2.

Methotrexate and all three conjugates inhibited FSAII proliferation. The minimum inhibitory concentration of the conjugates to inhibit proliferation was similar to or slightly higher than unconjugated methotrexate. There were no significant differences between minimum inhibitory concentrations of the three types of insulin-methotrexate conjugates.

The conjugates and methotrexate were also tested against other malignant cell lines including the human breast line MCF-7, the human prostate cancer line LNCAP, and the mouse mammary cancer line SCK. The results were very similar to those shown for FSAII (data not shown). Inhibition was also tested in rich medium, and the results were similar to those obtained in minimal medium (data not shown).

These results show that the insulin-MTX conjugates tested all were able to enter malignant cells and exert cytotoxic effect similar to methotrexate. This indicates the methotrexate portion of the conjugate is cleaved from the conjugate or is able to exert its cytotoxic effect while bound to the conjugate.

Example 2

Insulin and IGF Receptor Number and Cell Proliferation Response to Insulin and IGF-1

We analyzed several cancer cell lines for expression of IGF-1 receptors and insulin receptors on the cell surface. The cell lines tested were LNCAP (human prostate carcinoma), MCF-7 (human breast carcinoma), MDA-231 (human breast carcinoma), SCK (mouse mammary carcinoma), FSAII (mouse fibrosarcoma), and HOP-92 (human lung adenocarcinoma). Cells were contacted with fluorescently labeled antibodies recognizing the insulin and IGF-1 receptors and analyzed by flow cytometry, also known as Fluorescence Activated Cell Sorting (FACS).

Figure 3:
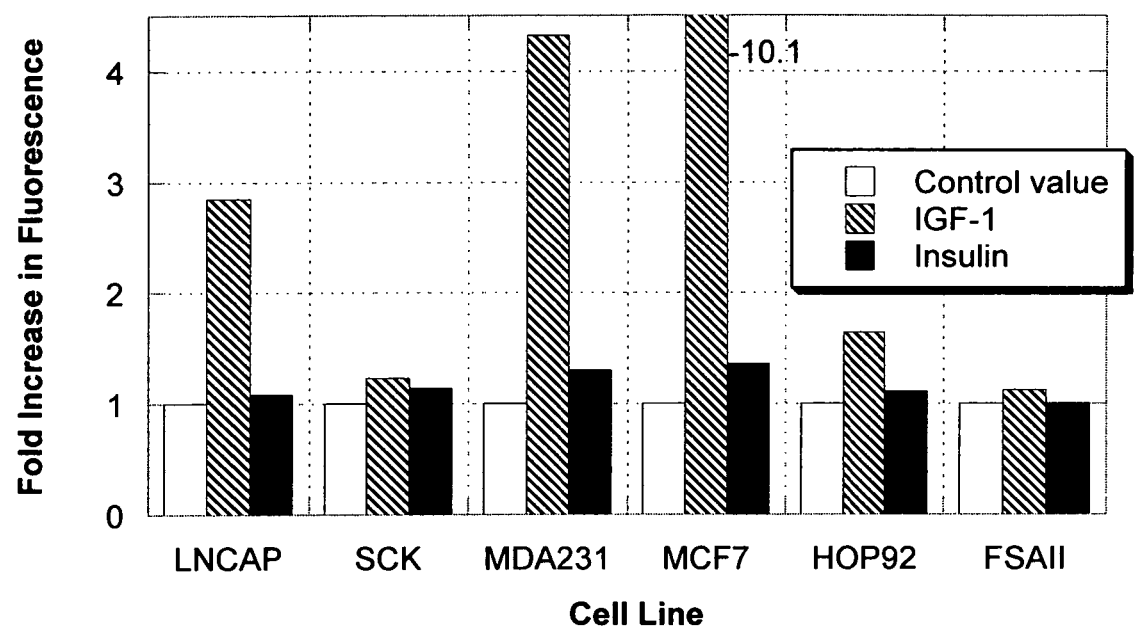
FIG. 3 is a plot showing the relative abundance of insulin receptors and IGF-1 receptors on several malignant cell lines based on fluorescence activated cell sorting (FACS) using fluorescently labeled antibodies against the receptors.

The results are shown in FIG. 3. The fluorescence value of the fixed cells not treated with the insulin or IGF receptor antibodies is fixed at 1. A fold increase of fluorescence of greater than 1 in the insulin or IGF bars indicates the presence of insulin or IGF receptors, and the relative abundance of the receptors can be compared between different cell lines. The results show all the cell lines had some insulin and IGF-1 receptors. IGF-1 receptors were more abundant than insulin receptors in all cell types. The two mouse cell lines SCK and FSAII appeared to have lower levels of insulin and IGF receptors than the human cell lines, but this could be an artifact from the fact that the antibodies used were antibodies against the human receptors.

The cell lines LNCAP, MCF-7, MDA-231, SCK, and HOP-92 were also tested to determine whether the cells increased their proliferation in the presence of insulin or IGF-1. Cells were plated in minimal medium with no addition (negative control), 1 ug/ml insulin, 100 ng/ml IGF-1, or 10% fetal calf serum (positive control), and cell density was monitored at 1, 2, and 4 days after plating. The data showed that both insulin and IGF-1 stimulated proliferation of all the cell lines except HOP-92. (Data not shown).

Example 3

In vivo Testing of a Methotrexate-Insulin Conjugate

The conjugate insulin-methotrexate-A, having approximately 3 methotrexate per insulin attached by direct amide bonds to amino groups on insulin was synthesized by the following procedure. Insulin (480 mg) was dissolved in 6 M urea, 25 mM sodium phosphate pH 7.4. Methotrexate (280 mg) was dissolved in the same buffer (with sodium hydroxide added to neutralize the acidic methotrexate and bring the pH up to 7.4) and mixed with the insulin in a final volume of 25 ml. Solid EDC (1.4 g) was added and the reaction was allowed to proceed at room temperature for 2 hours. After the reaction, a precipitate was formed which was solubilized by addition of glycine and NaOH to 50 mM glycine and pH 10.5. The product was passed 16 ml at a time through a 70 ml SEPHADEX G-25 column equilibrated with 50 mM glycine-NaOH, pH 10.5, to separate the conjugate product from unreacted methotrexate, urea, and other reagents. The purified product was found to contain 2.72 MTX per insulin by the absorbance at 372 nm. The product was mixed with glycerol to 10% w/v glycerol before freezing for storage.

Figure 4:
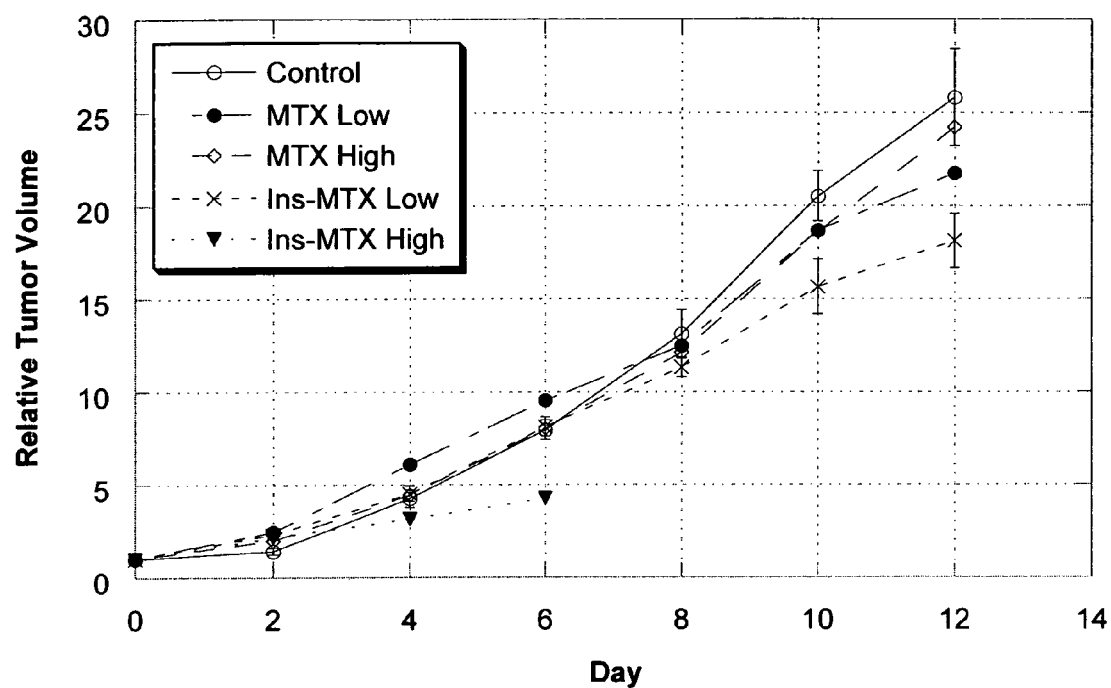
FIG. 4 is a plot showing the effects of methotrexate and an insulin-methotrexate conjugate in inhibiting FSAII tumor growth in vivo in mice. Standard error bars are shown for the untreated control data points and low dose insulin-methotrexate conjugate data points.

FSAII testing. Six-week old female mice were injected subcutaneously in the thigh with 200,000 FSAII cells each in serum-free medium. Tumors were allowed to grow until they reached an average volume of 100 $mm^3$ (calculated as length× $breadth^2$). At that time, treatment was initiated. Mice were injected intraperitoneally with 60 µmoles/kg (high dose) or 15 µmoles/kg (low dose) methotrexate in the form of unconjugated methotrexate or insulin-methotrexate-A conjugate. A fifth group of mice was untreated controls. Each group contained five mice. Mice were treated on days 0, 2, and 5. Tumor growth was measured every second day. The results are shown in FIG. 4.

Neither the high or low dose of methotrexate had any apparent effect on tumor growth. The low dose of the insulin-methotrexate conjugate significantly slowed tumor growth as compared to untreated controls. The high dose of the insulin-methotrexate conjugate appeared to very significantly slow tumor growth but was more toxic. It killed all five mice by one day following the third treatment.

Thus, the low dose of the conjugate was more effective than the high dose of unconjugated methotrexate. The conjugate was at least 4-fold more active against the FSAII tumors in vivo than unconjugated methotrexate.

Figure 5:
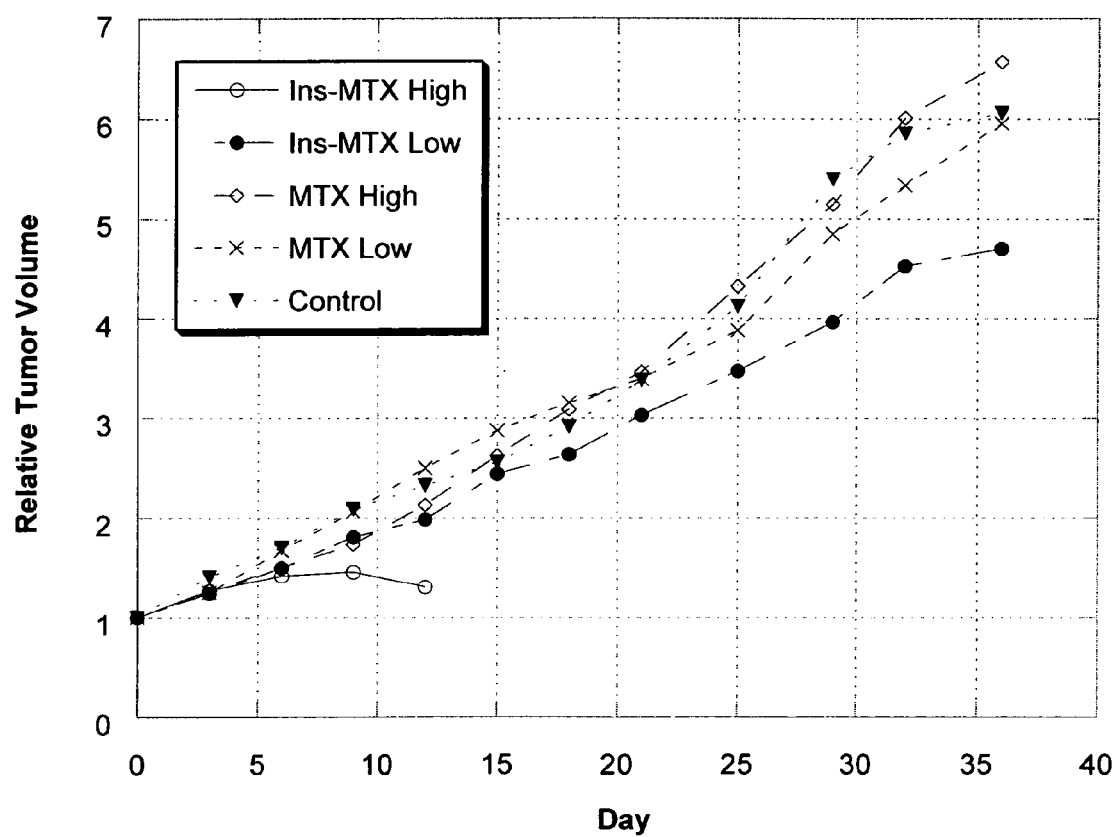
FIG. 5 is a plot showing the effects of methotrexate and an insulin-methotrexate conjugate in inhibiting LNCAP tumor growth in vivo in mice.

LNCAP testing. Eight-week old athymic male mice (nu/nu) were injected subcutaneously in the thigh with 1 million LNCAP cells in serum-free medium. Tumors were allowed to grow until they reached an average size of 100 mm$^3$. Mice were then treated on days 0, 4, and 8, and again on days 18, 22, and 26 with 40 μmoles/kg (high dose) or 15 μmoles/kg (low dose) methotrexate in the form of unconjugated methotrexate or insulin-methotrexate-A conjugate. A fifth group of mice was untreated controls. The results are shown in FIG. 5.

The results were similar to the results with FSA. The low dose insulin-methotrexate conjugate appeared to slow tumor growth, while the high and low dose unconjugated methotrexate appeared to have no effect. The high dose insulin-methotrexate conjugate was toxic despite the slightly lower dose and greater time between doses that was used in this experiment as compared to the FSAII experiment.

Conclusions: The insulin-methotrexate conjugate was effective at at least 4-fold lower concentration than unconjugated methotrexate against FSAII tumors in mice and at at least 2.6 times lower concentration than unconjugated methotrexate against LNCAP tumors in mice.

Example 4

Synthesis of an IGF-Methotrexate Conjugate

This conjugate was a conjugate of methotrexate to a variant of IGF-1 called LONG-R3-IGF-1 (GroPep, Ltd., Australia). LONG-R3-IGF has the first 11 residues of methionyl porcine growth hormone followed by Val-Asn and the human IGF-1 sequence with and Arg substituted at position 3 of the IGF-1 sequence. Its sequence is SEQ ID NO:4. LONG-R3-IGF-1 has reduced binding affinity for soluble IGF binding proteins but equal binding affinity for the type 1 IGF receptor and equal or greater biological activity as compared to wild-type IGF-1 (Francis, G. L., et al.1992, *J. Mol. Endocrinol.* 8:213-223; Tomas, F. M. et al., 1993, *J. Endocrinol.* 137:413-421).

LONG-R3-IGF-1 (1.5 mg) was dissolved in 0.3 ml of 10 mM HCl. It was dialyzed against 25 mM sodium phosphate, 10 mM NaCl, 6.3 M urea, pH 7.4, overnight. Then 84 μl MTX in the same buffer was added to the sample in the dialysis bag (3,000 m.w. cutoff). Then 15 mg EDC freshly dissolved in the same buffer was added. The sample in the dialysis bag was placed in a dish in air to react for 2 hours at room temperature. Then the bag was placed again in the same dialysis buffer and dialyzed overnight to remove unreacted methotrexate and other reagents. Then the sample was dialyzed for 12 hours against 25 mM sodium phosphate, pH 7.4. The product precipitated following this dialysis. Next, the dialysis bag was placed in 10 mM HCl, which solubilized the product. Optical absorbance at 372 nm of the sample was determined diluted into pH 7.4 buffer to quantify methotrexate in the conjugate. The conjugate was determined to contain 2.94 MTX per LONG-R3-IGF-1 by this method, using $\epsilon_{372\,nm}=6.85$ mM$^{-1}$ for methotrexate.

Example 5

In vitro Cytotoxic Activity of the Methotrexate-IGF-1 Conjugate

Figure 6:
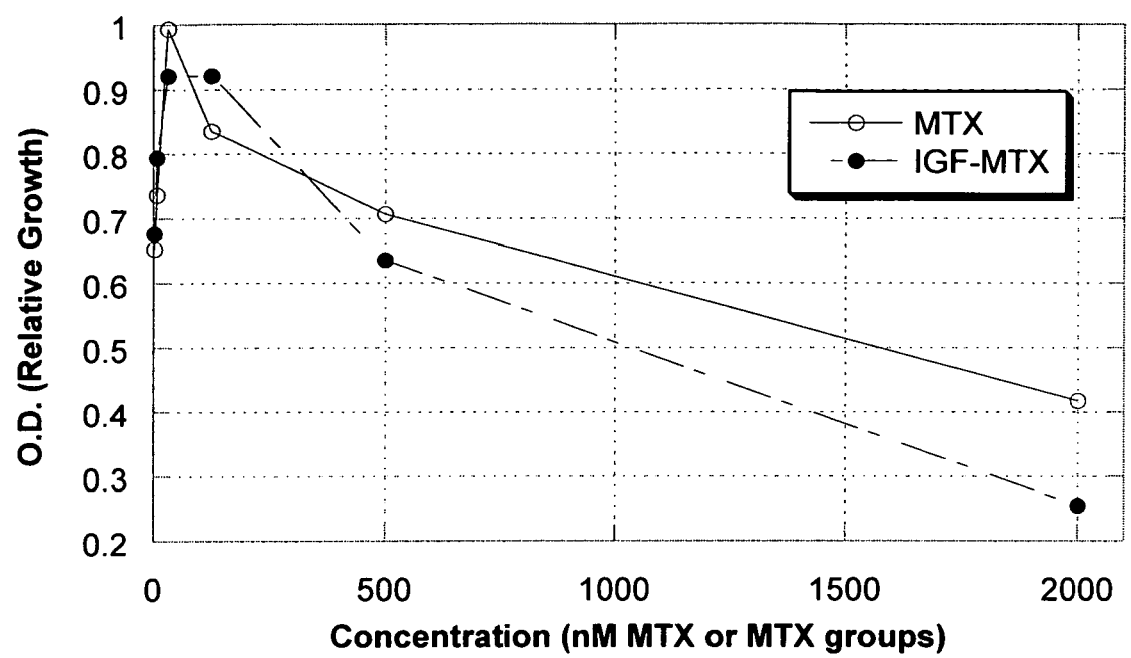
FIG. 6 is a plot showing the concentration dependence of in vitro growth inhibition of LNCAP tumor cells by methotrexate and a LONG-R3-IGF-1-methotrexate conjugate.

The IGF-methotrexate conjugate of Example 5 was tested for inhibition of tumor cell proliferation in vitro against LNCAP cells. LNCAP cells were plated in a 96-well plate at 3,000 cells per well in RPMI medium supplemented with 10% fetal bovine serum (FBS). After incubation overnight, the medium in the wells was replaced with 100 μl per well of RPMI supplemented with 0.1% FBS. The conjugate and unconjugated methotrexate were added to the wells in triplicate at concentrations ranging from 2 nM to 2 μM. After incubation for 4 days, cell proliferation was assayed with the cell counting kit-8 (Dojindo Molecular Technologies, Gaithersburg, Md.). The results are shown in FIG. 6. The IGF-MTX conjugate and unconjugated methotrexate both inhibited growth with a minimum inhibitory concentration of approximately 500 nM to 2 μM. Similar results were obtained with proliferation assays in rich medium containing 10% FBS (Table 1).

The data of Table 1 also show that the minimal inhibitory concentration of unconjugated methotrexate in minimal medium containing 0.1% serum was about 2000 nM, whereas in rich medium containing 10% serum it was about 125 nM. Thus, serum, with its growth factors including IGF-1 and insulin, substantially decreased the concentration of methotrexate needed to inhibit growth of LNCAP tumor cells.

TABLE 1

LNCAP proliferation in vitro.

| MTX conc. (nM) | Cell number (relative units) | | | |
|---|---|---|---|---|
| | MTX Rich medium | IGF-MTX conjugate Rich medium | MTX Minimal med. | IGF-MTX conjugate Minimal med. |
| 2000 | 0.147 ± .005 | 0.234 ± .004 | 0.418 ± .026 | .255 ± .014 |
| 500 | 0.163 ± .009 | 0.381 ± .008 | .706 ± .051 | .635 ± .038 |
| 125 | 0.223 ± .012 | 0.891 ± .017 | .835 ± .048 | .921 ± .014 |
| 32 | 1.017 ± .033 | 1.248 ± .018 | .994 ± .226 | .921 ± .014 |
| 8 | 0.596 ± .071 | 0.674 ± .036 | .737 ± .043 | .794 ± .028 |
| 2 | 0.724 ± .015 | 0.716 ± .021 | .653 ± .046 | .677 ± .057 |

Example 6

Methotrexate Activity in Human Breast Cancer Model, where Methotrexate is Coupled to Insulin, IGF-1, or IGF-2, or Coadministered with Insulin or IGF-1

In vitro Testing:

MCF-7 is a human breast cancer cell line that is responsive to both insulin and IGF-1 (Alabaster, O., et al., 1981, *Eur J Cancer Clin. Oncol.* 17: 1223-1228; Dupont, J., et al., 2003, *J. Biol. Chem.* 278:37256).

MCF-7 cells are cultured in F12/DME medium supplemented with 5% fetal calf serum (FCS) in 95% air, 5% $CO_2$ at 37° C. (Karey, K. P. et al., 1988, *Cancer Res.* 48:4083-4092.) Cells are transferred every 4-6 days and seeded at 1.75×10$^6$ cells/plate in 20 ml medium in a 10 cm dish. For the assays, the cells were washed with sterile saline, detached from the plate in 3 ml of trypsin-EDTA in Hank's buffered salt solution. After cells are detached from the plate (2-4 minutes at room temperature), the trypsin is inactivated by the addition of 4 ml of PBS containing 0.1% soybean trypsin inhibitor. The cells are then washed three times in Tf/BSA (F12/DME supplemented with 10 μg/ml transferrin and 200 μg/ml bovine serum albumin). Cells are seeded at 1,000-20,000 cells in 2 ml of Tf/BSA medium in 35 mm diameter culture plates. Twenty-four hours after plating, the cells are treated with MTX ($10^{-10}$-$10^{-3}$ M), MTX and insulin, MTX and IGF-1, at a range of methotrexate concentrations. The concentration of unconjugated IGF-1 is 50 ng/ml when present. The concentration of unconjugated insulin is 1 μg/ml when present. Controls treated with no agent, insulin, or IGF-1 or with 5% FCS are also conducted.

Total cells are counted by microscopy and live cell number is determined by Trypan blue staining on the 7th day of culture (after 6 days of exposure to MTX or the other agents).

The $IC_{50}$ of MTX for inhibition of cell growth is determined under each of the tested conditions. It is determined that when administered with insulin or IGF-1, lower concentrations of MTX are needed to achieve the same extent of inhibition of cell growth.

In vivo Testing:

MCF-7 cells are cultured as described above. Six-week-old female nude mice (nu/nu, Sprague Dawley, Madison, Wis.) are injected subcutaneously in the back with $5 \times 10^6$ MCF-7 cells in 0.05 ml serum-free medium. Estrogen production in the mice is inadequate to support growth of MCF-7, so the mice are given injections of beta-estradiol dissolved in sesame oil (0.1 mg/0.05 ml oil s.c.) beginning one day before injection of the cancer cells and weekly thereafter. Tumors are allowed to grow until a diameter of 5 mm. (Hardman, W. E., et al., 1999, *Anticancer Res.* 19:2269.)

When tumors reach a diameter of 5 mm, mice are treated once daily with MTX over a range of concentrations, or the mice are treated with insulin or IGF-1, and then 30 minutes later with MTX over a range of concentrations. The mice are fasted for 4 hours prior to treatment, and are given access to food immediately after treatment. Tumor size is measured by calipers twice weekly.

It is found that equal or better tumor shrinkage is achieved with lower doses of methotrexate when the methotrexate is administered in conjunction with insulin or IGF-1. This allows the same or better killing of tumors with lower side effects.

Example 7

Doxorubicin Activity in Human Colon Cancer Model, where Doxorubicin is Coupled to Insulin, IGF-1, or IGF-2, or Coadministered with Insulin or IGF-1

In vitro Testing:

HT29 is a human colorectal cancer cell line that is responsive to insulin and IGF-1 (Riera, L., et al., 2002, *Biochim. Biophys. Acta* 1589:89; Valee, S., et al., 2003, *Biochem. Biophys. Res. Commun.* 305:831).

Doxorubicin-insulin, doxorubicin-IGF-1, and doxorubicin-IGF-2 conjugates with approximately one doxorubicin per protein molecule are prepared as described in Synthetic Example 2.

HT29 cells are grown in RPMI 1640 medium supplemented with 10% fetal calf serum. Confluent cells are trypsinized, washed, and cultured in Tf/BSA (minimal medium) as described in Example 6. After 1 day of adaptation to the minimal medium, doxorubicin, doxorubicin and insulin, doxorubicin and IGF-1, the doxorubicin-insulin conjugate, the doxorubicin-IGF-1 conjugate, or the doxorubicin-IGF-2 conjugate at a range of concentrations is added to each plate. Doxorubicin, for instance, is at a range of about 0.1 µM to about 50 µM final concentration in the wells. Free IGF-1 is at a concentration of about 10 nM. Unconjugated insulin is at a concentration of about 1 µM. Controls treated with no agent, insulin, or IGF-1 or with 5% FCS are also conducted.

After 7 days of growth (6 days in the tested chemotherapeutic agents) total and live cell number is determined as described in Example 1.

The $IC_{50}$ of doxorubicin and each of the conjugates for inhibition of cell growth is determined under each of the tested conditions. It is determined that when administered with insulin or IGF-1, lower concentrations of doxorubicin are needed to achieve the same extent of cell growth inhibition. It is also determined that the $IC_{50}$s of doxorubicin-insulin, doxorubicin-IGF-1, and doxorubicin-IGF-2 are lower than or similar to the $IC_{50}$ of free doxorubicin.

In vivo Testing:

HT29 cells are cultured as described above. Six-week-old female nude mice are injected subcutaneously in the flanks with $10^7$ HT29 cells. Tumors are allowed to grow to a diameter of 5 mm.

When tumors reach a diameter of 5 mm, mice are treated once daily with one of the agents doxorubicin, doxorubicin-insulin, doxorubicin-IGF-1, or doxorubicin-IGF-2. Or the mice are treated with insulin or IGF-1, and then 30 minutes later with doxorubicin. The mice are fasted for 4 hours prior to treatment, and are given access to food immediately after treatment. Tumor size is measured by calipers twice weekly.

It is found that equal or better tumor shrinkage is achieved with lower doses of doxorubicin when the doxorubicin is administered in conjunction with insulin, IGF-1, or IGF-2, or when it is administered as part of a conjugate with insulin, IGF-1, or IGF-2. This allows better killing of tumors or allows equivalent killing of tumors with lower side effects.

All patents, patent documents, and references cited herein are incorporated by reference.

What is claimed is:

1. A compound for treating cancer comprising:
   an anti-cancer chemotherapeutic agent linked to
   an insulin-like growth factor-1 (IGF-1) receptor ligand;
   wherein the IGF-1 receptor ligand is a variant IGF-1 that has reduced binding affinity for soluble IGF-1 binding proteins compared to wild-type IGF-1;
   wherein the variant IGF-1 comprises the polypeptide structure $A_1$-$A_2$-$A_3$-$A_4$-LCG-$A_5$-$A_6$-LV-$A_7$-AL-$A_8$-$A_9$-$R_1$, wherein
   A1 is FV;
   A2 is N;
   A3 is Q;
   A4 is H;
   A5 is S;
   A6 is H;
   A7 is E;
   A8 is Y;
   A9 is L; and
   R1 is SEQ ID NO:6;
   provided the variant IGF-1 does not consist of SEQ ID NO:1.

2. The compound of claim 1 wherein the chemotherapeutic agent is amsacrine, azacytidine, bleomycin, busulfan, capecitabine, carboplatin, carmustine, chlorambucil, cisplatin, cladribine, cyclophosphamide, cytarabine, dactinomycin, daunorubicin, decarbazine, docetaxel, doxorubicin, epirubicin, estramustine, etoposide, floxuridine, fludarabine, fluorouracil, gemcitabine, hexamethylmelamine, idarubicin, ifosfamide, irinotecan, lomustine, mechlorethamine, melphalan, mercaptopurine, methotrexate, mitomycin C, mitotane, mitoxantrone, oxaliplatin, paclitaxel, pemetrexed, pentostatin, plicamycin, procarbazine, ralitrexed, semustine, streptozocin, temozolamide, teniposide, thioguanine, thiotepa, topotecan, trimitrexate, valrubicin, vincristine, vinblastine, vindestine, or vinorelbine.

3. The compound of claim 1 wherein the chemotherapeutic agent is an anti-metabolite.

4. The compound of claim 1 wherein the anti-cancer chemotherapeutic agent is linked to the IGF-1 receptor ligand by a linkage comprising an amide bond.

5. The compound of claim 1 wherein the anti-cancer chemotherapeutic agent is linked to the variant IGF-1 through an amino group of the variant IGF-1.

6. The compound of claim 3 wherein the anti-metabolite is methotrexate.

7. The compound of claim 1 wherein the anti-cancer chemotherapeutic agent is doxorubicin.

8. A pharmaceutical composition comprising a compound of claim 1.

9. A compound for treating cancer comprising:
   an anti-cancer chemotherapeutic agent linked to an insulin-like growth factor-1 (IGF-1) receptor ligand;
   wherein the IGF-1 receptor ligand is a variant IGF-1 that has reduced binding affinity for soluble IGF-1 binding proteins compared to wild-type IGF-1;
   wherein the variant IGF-1 comprises SEQ ID NO:7, SEQ ID NO:8, SEQ ID NO:9, or SEQ ID NO:10.

10. The compound of claim 9 wherein the variant IGF-1 is SEQ ID NO:4.

11. The compound of claim 9 wherein the chemotherapeutic agent is amsacrine, azacytidine, bleomycin, busulfan, capecitabine, carboplatin, carmustine, chlorambucil, cisplatin, cladribine, cyclophosphamide, cytarabine, dactinomycin, daunorubicin, decarbazine, docetaxel, doxorubicin, epirubicin, estramustine, etoposide, floxuridine, fludarabine, fluorouracil, gemcitabine, hexamethylmelamine, idarubicin, ifosfamide, irinotecan, lomustine, mechlorethamine, melphalan, mercaptopurine, methotrexate, mitomycin C, mitotane, mitoxantrone, oxaliplatin, paclitaxel, pemetrexed, pentostatin, plicamycin, procarbazine, ralitrexed, semustine, streptozocin, temozolamide, teniposide, thioguanine, thiotepa, topotecan, trimitrexate, valrubicin, vincristine, vinblastine, vindestine, or vinorelbine.

12. The compound of claim 9 wherein the chemotherapeutic agent is an anti-metabolite.

13. The compound of claim 9 wherein the anti-cancer chemotherapeutic agent is linked to the IGF-1 receptor ligand by a linkage comprising an amide bond.

14. The compound of claim 9 wherein the anti-cancer chemotherapeutic agent is linked to the variant IGF-1 through an amino group of the variant IGF-1.

15. The compound of claim 12 wherein the anti-metabolite is methotrexate.

16. The compound of claim 9 wherein the anti-cancer chemotherapeutic agent is doxorubicin.

17. pharmaceutical composition comprising a compound of claim 9.

* * * * *